(12) United States Patent
Lutz et al.

(10) Patent No.: US 12,201,693 B2
(45) Date of Patent: *Jan. 21, 2025

(54) AMANITIN CONJUGATES

(71) Applicant: Heidelberg Pharma Research GmbH, Ladenburg (DE)

(72) Inventors: Christian Lutz, Weinheim (DE); Jan Anderl, Modautal (DE); Christoph Mueller, Birkenau (DE); Werner Simon, Hueffelsheim (DE); Susanne Werner-Simon, Hueffelsheim (DE); Torsten Hechler, Lautertal (DE); Michael Kulke, Ludwigshafen (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/175,148

(22) Filed: Feb. 27, 2023

(65) Prior Publication Data
US 2023/0233703 A1    Jul. 27, 2023

Related U.S. Application Data

(63) Continuation of application No. 16/081,400, filed as application No. PCT/EP2017/054911 on Mar. 2, 2017, now Pat. No. 11,590,238.

(30) Foreign Application Priority Data

Mar. 3, 2016    (EP) ..................................... 16000511

(51) Int. Cl.
A61K 47/68    (2017.01)
C07K 16/30    (2006.01)

(52) U.S. Cl.
CPC ...... *A61K 47/6831* (2017.08); *A61K 47/6851* (2017.08); *C07K 16/30* (2013.01)

(58) Field of Classification Search
None
See application file for complete search history.

(56) References Cited

U.S. PATENT DOCUMENTS 10,842,882 B2    11/2020    Anderl
2017/0252300 A1    9/2017    Modi

FOREIGN PATENT DOCUMENTS

| CL | 200001195 A1 | 5/2000 |
| CL | 200900505 A1 | 1/2010 |
| CL | 201500529 A1 | 11/2015 |
| CL | 201802474 A1 | 1/2019 |

(Continued)

OTHER PUBLICATIONS

Zhao et al., ChemBioChem 2015, 16, 1420-1425 (Year: 2015).*

(Continued)

*Primary Examiner* — Karl J Puttlitz
(74) *Attorney, Agent, or Firm* — McBee, Moore & Vanik IP, LLC

(57) ABSTRACT

The invention relates to a conjugate comprising (a) an amatoxin comprising (i) an amino acid 4 with a 6'-deoxy position; and (ii) an amino acid 8 with an S-deoxy position; (b) a target-binding moiety; and (c) optionally a linker linking said amatoxin and said target-binding moiety. The invention furthermore relates to a pharmaceutical composition comprising such conjugate.

5 Claims, 14 Drawing Sheets

| | R₁ | R₂ | R₃ | R₄ |
|---|---|---|---|---|
| α-amanitin | OH | OH | NH₂ | OH |
| β-amanitin | OH | OH | OH | OH |
| γ-amanitin | H | OH | NH₂ | OH |
| ε-amanitin | H | OH | OH | OH |
| amanin | OH | OH | OH | H |
| amaninamide | OH | OH | NH₂ | H |
| amanullin | H | H | NH₂ | OH |
| amanullinic acid | H | H | OH | OH |
| γ-amanin | H | OH | OH | H |
| γ-amaninamide | H | OH | NH₂ | H |

(56) References Cited

FOREIGN PATENT DOCUMENTS

| EP | 1859811 A1 | 11/2007 |
| JP | 2015519906 A | 7/2015 |
| JP | 2015533490 A | 11/2015 |
| WO | 00/71571 A2 | 11/2000 |
| WO | 2009/111653 A2 | 9/2009 |
| WO | 2013184514 A1 | 12/2013 |
| WO | 2014/043068 A1 | 3/2014 |
| WO | 2014043361 A1 | 3/2014 |

OTHER PUBLICATIONS

International Search Report, International Application No. PCT/EP2017/054911 (published under WO 2017/149077) 11 pages (May 17, 2017).

Written Opinion, International Application No. PCT/EP2017/054911 (published under WO 2017/149077) 6 pages (Feb. 20, 2018).

Zhao et al., "Synthesis of a Cytotoxic Amanitin for Biorthogonal Conjugation," ChemBioChem, vol. 16, No. 10, pp. 1420-1425 (Jun. 3, 2015).

\* cited by examiner

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |
| γ-amanin | H | OH | OH | H |
| γ-amaninamide | H | OH | NH2 | H |

Cytotoxicity on SKBR-3 cells after incubation in Human plasma

Cytotoxicity on SKBR-3 cells after incubation in Mouse plasma

AMANITIN CONJUGATES

CROSS-REFERENCE TO RELATED APPLICATIONS

This application is a continuation of U.S. application Ser. No. 16/081,400 filed on Aug. 30, 2018, which is a 371 National Phase of International Patent Application No. PCT/EP2017/054911 filed on Mar. 2, 2017, which claims priority to European Application No. EP16000511.2 filed on Mar. 3, 2016, the content of each of which applications is incorporated herein by reference.

FIELD OF THE INVENTION

The invention relates to a conjugate comprising (a) an amatoxin comprising (i) an amino acid 4 with a 6'-deoxy position; and (ii) an amino acid 8 with an S-deoxy position; (b) a target-binding moiety; and (c) optionally a linker linking said amatoxin and said target-binding moiety. The invention furthermore relates to a pharmaceutical composition comprising such conjugate.

BACKGROUND OF THE INVENTION

Amatoxins are cyclic peptides composed of 8 amino acids that are found in *Amanita phailoides* mushrooms (see FIG. 1). Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight ($K_D$=3 nM). Dissociation of amanitin from the enzyme is a very slow process, thus making recovery of an affected cell unlikely. When the inhibition of transcription lasts too long, the cell will undergo programmed cell death (apoptosis).

The use of amatoxins as cytotoxic moieties for tumour therapy had already been explored in 1981 by coupling an anti-Thy 1.2 antibody to α-amanitin using a linker attached to the indole ring of Trp (amino acid 4; see FIG. 1) via diazotation (Davis & Preston, Science 213 (1981) 1385-1388). Davis & Preston identified the site of attachment as position 7'. Morris & Venton demonstrated as well that substitution at position 7' results in a derivative, which maintains cytotoxic activity (Morris & Venton, Int. J. Peptide Protein Res. 21 (1983) 419-430).

Patent application EP 1 859 811 A1 (published Nov. 28, 2007) described conjugates, in which the γ C-atom of amatoxin amino acid 1 of β-amanitin was directly coupled, i.e. without a linker structure, to albumin or to monoclonal antibody HEA125, OKT3, or PA-1. Furthermore, the inhibitory effect of these conjugates on the proliferation of breast cancer cells (MCF-7), Burkitt's lymphoma cells (Raji) and T-lymphoma cells (Jurkat) was shown. The use of linkers was suggested, including linkers comprising elements such as amide, ester, ether, thioether, disulfide, urea, thiourea, hydrocarbon moieties and the like, but no such constructs were actually shown, and no more details, such as attachment sites on the amatoxins, were provided.

Patent applications WO 2010/115629 and WO 2010/115630 (both published Oct. 14, 2010) describe conjugates, where antibodies, such as anti-EpCAM antibodies such as humanized antibody huHEA125, are coupled to amatoxins via (i) the γ C-atom of amatoxin amino acid 1, (ii) the 6' C-atom of amatoxin amino acid 4, or (iii) via the δ C-atom of amatoxin amino acid 3, in each case either directly or via a linker between the antibody and the amatoxins. The suggested linkers comprise elements such as amide, ester, ether, thioether, disulfide, urea, thiourea, hydrocarbon moieties and the like. Furthermore, the inhibitory effects of these conjugates on the proliferation of breast cancer cells (cell line MCF-7), pancreatic carcinoma (cell line Capan-1), colon cancer (cell line Colo205), and cholangiocarcinoma (cell line OZ) were shown.

Patent application WO 2012/119787 describes that target-binding moieties can be attached to amatoxins via linkers at additional attachment sites on tryptophan amino acid 4, namely positions 1'-N, without interference with the interaction of such amatoxins with their target, the DNA-dependent RNA polymerase II of mammalian cells.

It is known that amatoxins are relatively non-toxic when coupled to large biomolecule carriers, such as antibody molecules, and that they exert their cytotoxic activity only after the biomolecule carrier is cleaved off. In light of the toxicity of amatoxins, particularly for liver cells, it is of outmost importance that amatoxin conjugates for targeted tumour therapy remain highly stable after administration in plasma, and that the release of the amatoxin occurs after internalization in the target cells. In this context, minor improvements of the conjugate stability may have drastic consequences for the therapeutic window and the safety of the amatoxin conjugates for therapeutic approaches.

Patent application WO 2012/041504 describes conjugates of an amatoxin with a binding molecule, which use a urea moiety as linker to the binding molecule. Such linkage could be shown to be significantly more stable than an ester linkage.

Thus, significant progress has already been made in the development of amatoxin-based conjugates for therapeutic uses. However, the present inventors have found that constructs based on α- and β-amatoxin were not fully stable under stress conditions in plasma and resulted in a substantial degree of cross-linked products (see FIGS. 2 to 4). However, the stability of the conjugates comprising a highly toxic amatoxin is of utmost importance for the envisaged use as a therapeutic molecule for administration to human beings.

OBJECT OF THE INVENTION

Thus, there was still a great need for amatoxin variants with an improved stability. The solution to this problem, i.e. the identification of certain modifications to the backbone of eight amino acid residues forming the basic amatoxin structure was neither provided nor suggested by the prior art.

SUMMARY OF THE INVENTION

The present invention is based on the unexpected observation that a variant form of amatoxins with (i) an amino acid 4 with a 6'-deoxy position; and (ii) an amino acid 8 with an S-deoxy position, shows an increased stability under stress conditions and an improved therapeutic index.

Thus, in one aspect the present invention relates to a conjugate comprising (a) an amatoxin comprising (i) an amino acid 4 with a 6'-deoxy position; and (ii) an amino acid 8 with an S-deoxy position; (b) a target-binding moiety; and (c) optionally a linker linking said amatoxin and said target-binding moiety. In particular, the optional linker of (c) is present and is a cleavable linker.

In a second aspect, the present invention relates to a pharmaceutical composition comprising the conjugate of the present invention.

In a third aspect, the present invention relates to a conjugate of the present invention for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, leukemia, and malignant lymphoma.

In a fourth aspect, the present invention relates to a construct comprising (a) an amatoxin comprising (i) an amino acid 4 with a 6'-deoxy position; and (ii) an amino acid 8 with an S-deoxy position; and (c) a linker moiety, particularly a linker that is cleavable, carrying a reactive group for linking said amatoxin to a target-binding moiety.

DETAILED DESCRIPTION OF THE INVENTION

Figure 1:
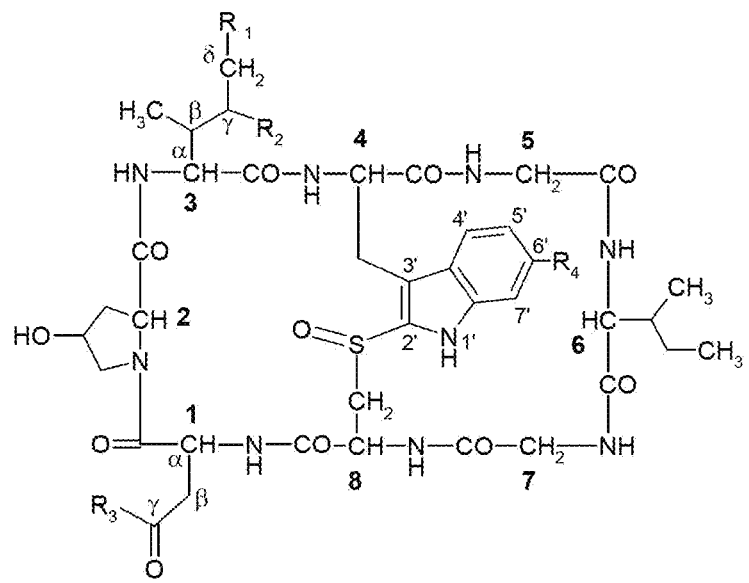
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).
Figure 2:
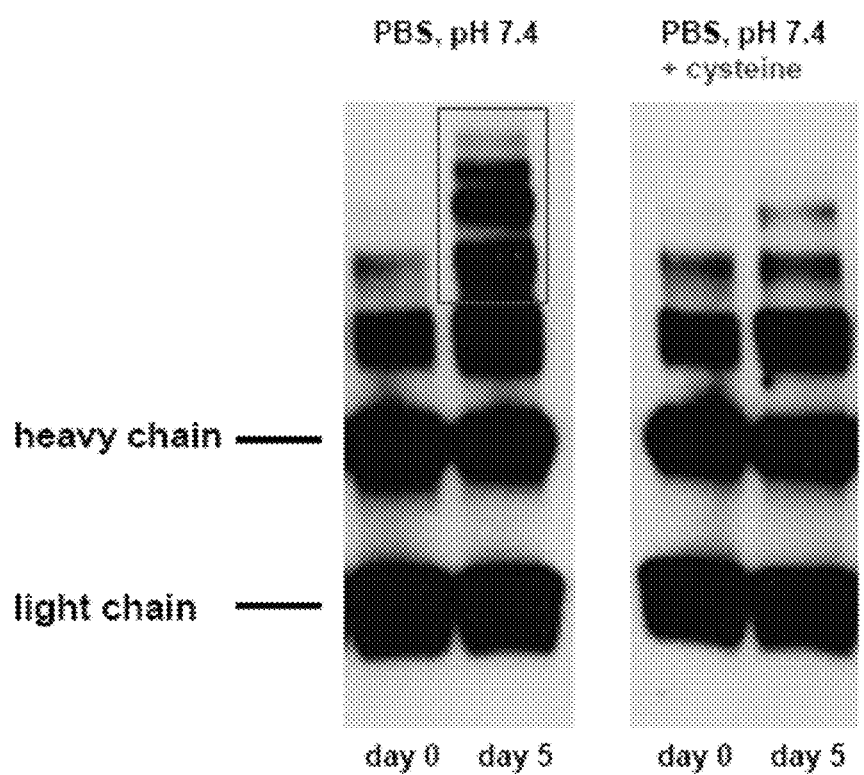
FIG. 2 shows the results of a stress testing experiment in an anti-amanitin Western blot. A trastuzumab-amanitin conjugate (Her-30.0643; lysine conjugation via 6'-OH; stable linker) was incubated for 5 days at 37° C. in PBS, pH 7.4, which led to extensive inter- and intrachain cross-linking; cross-linking of antibody chains could be prevented by addition of free cysteine.
Figure 3:
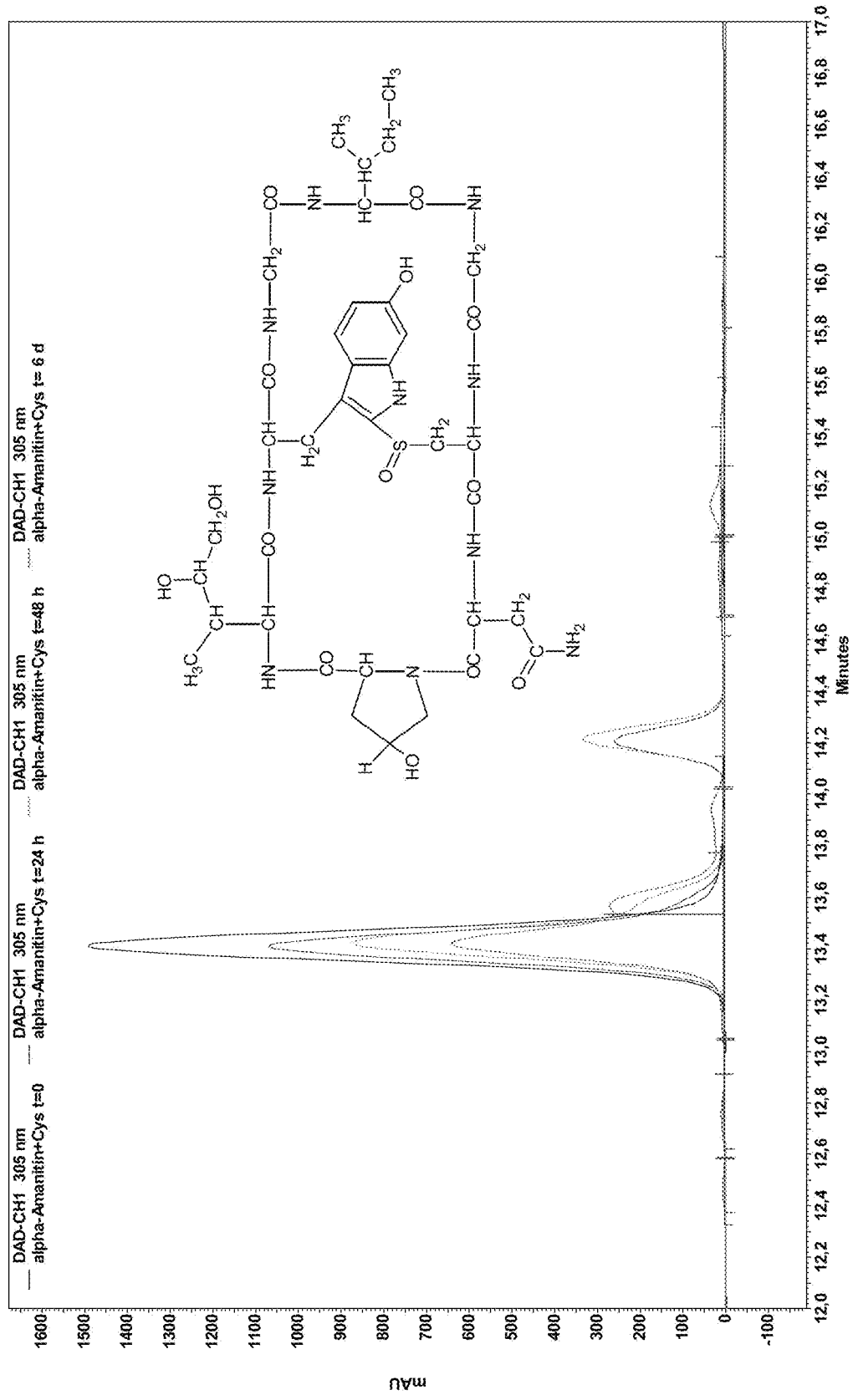
FIG. 3 shows that α-Amanitin shows a strong reactivity with cysteine in PBS buffer, pH 7.4. 1 mg/ml α-amanitin 10 mg/mL cysteine in PBS, pH 7.4 at 37° C. after 24 h, 48 h and 6 d RP-HPLC C18.
Figure 4:
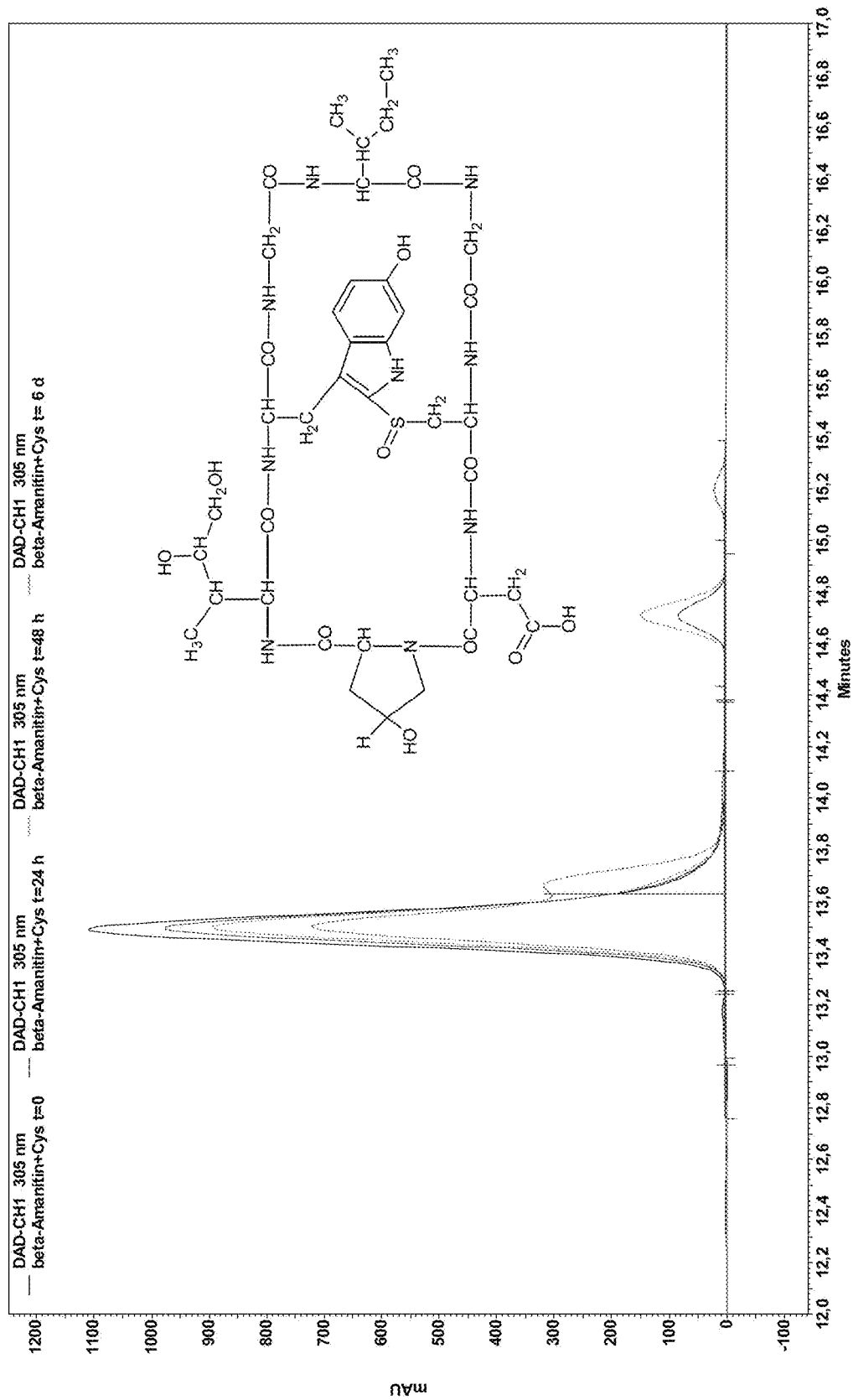
FIG. 4 shows that β-Amanitin shows a strong reactivity with cysteine in PBS buffer, pH 7.4. 1 mg/mL β-amanitin 10 mg/mL cysteine in PBS, pH 7.4 at 37° C. after 24 h, 48 h and 6 d RP-HPLC 018.
Figure 5:
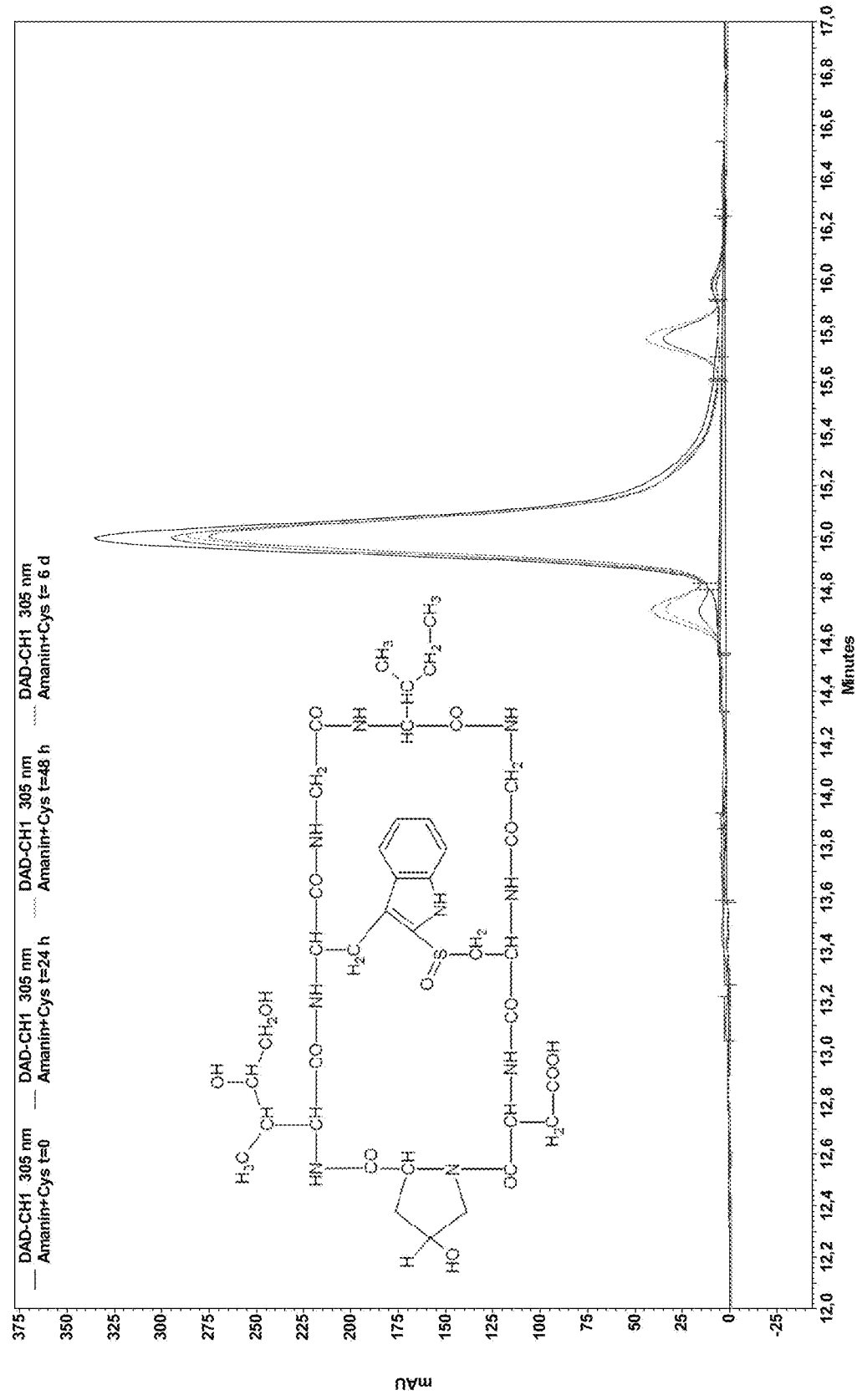
FIG. 5 shows that a 6"-deoxy variant at amino acid 4 ("amanin") shows a reduced reactivity with cysteine. 1 mg/mL amanin 10 mg/mL cysteine in PBS, pH 7.4 at 37° C. after 24 h, 48 h and 6 d RP-HPLC 018.
Figure 6:
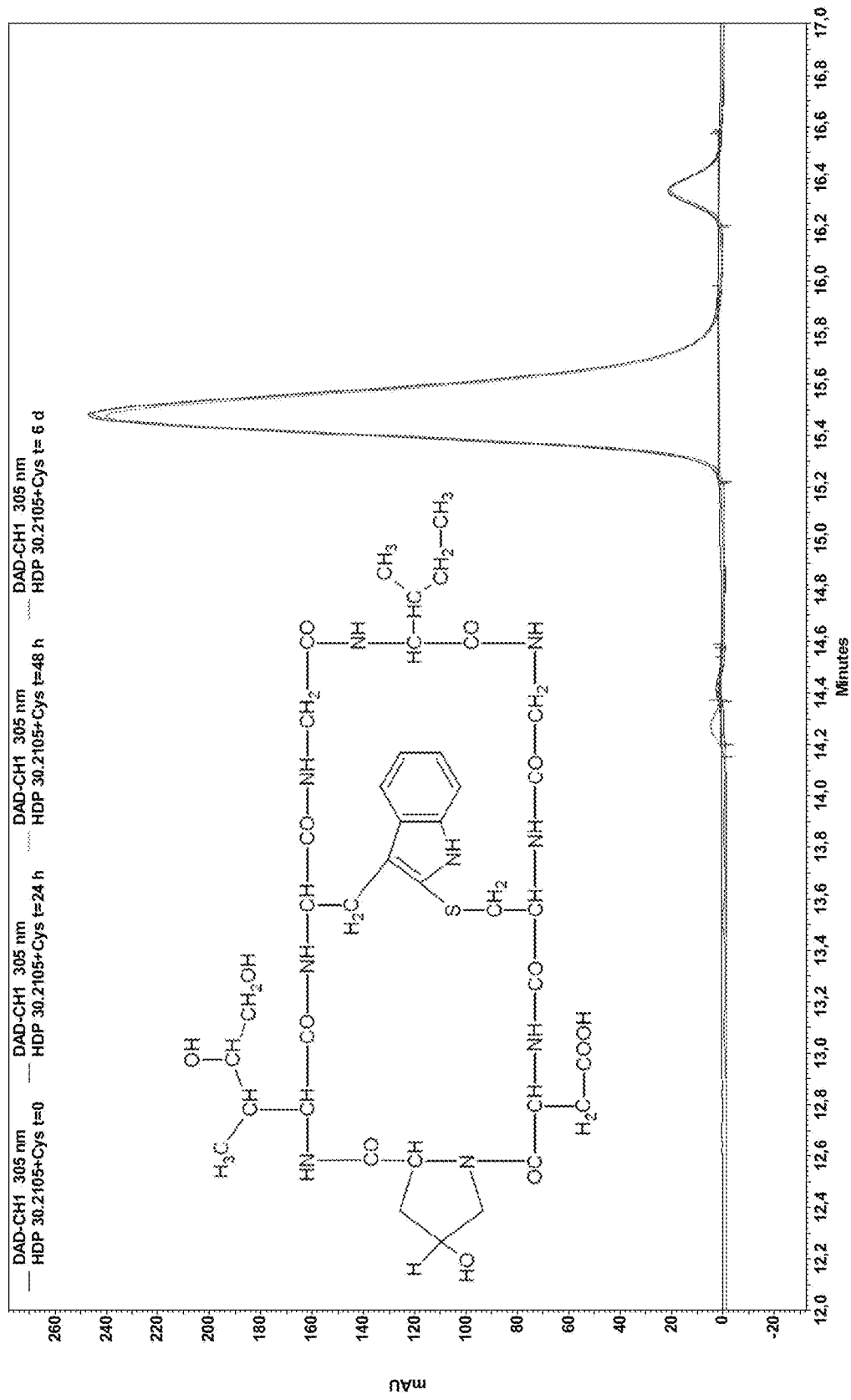
FIG. 6 and FIG. 7 show that a double deoxy variant HDP 30.2105 (6'-deoxy at amino acid 4 and S-deoxy at amino acid 8; formula I with $R^3$=—$OR^5$ and each $R^5$=H) shows complete absence of reactivity with cysteine. 1 mg/mL HDP 30.2105, 10 mg/mL cysteine in PBS, pH 7.4 at 37° C. after 24 h, 48 h and 6 d RP-HPLC C18; * impurity.
Figure 7:
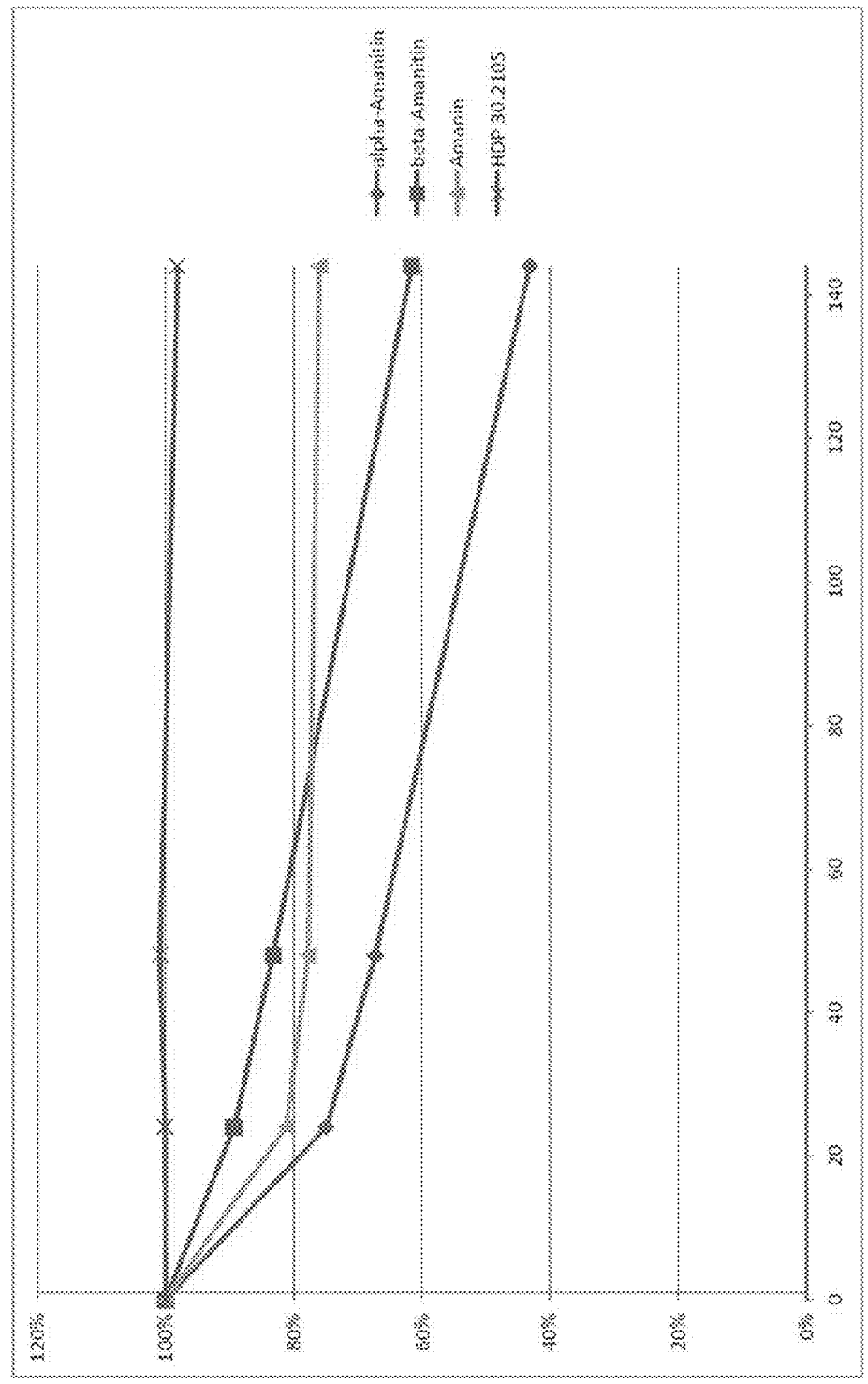
Figure 8:
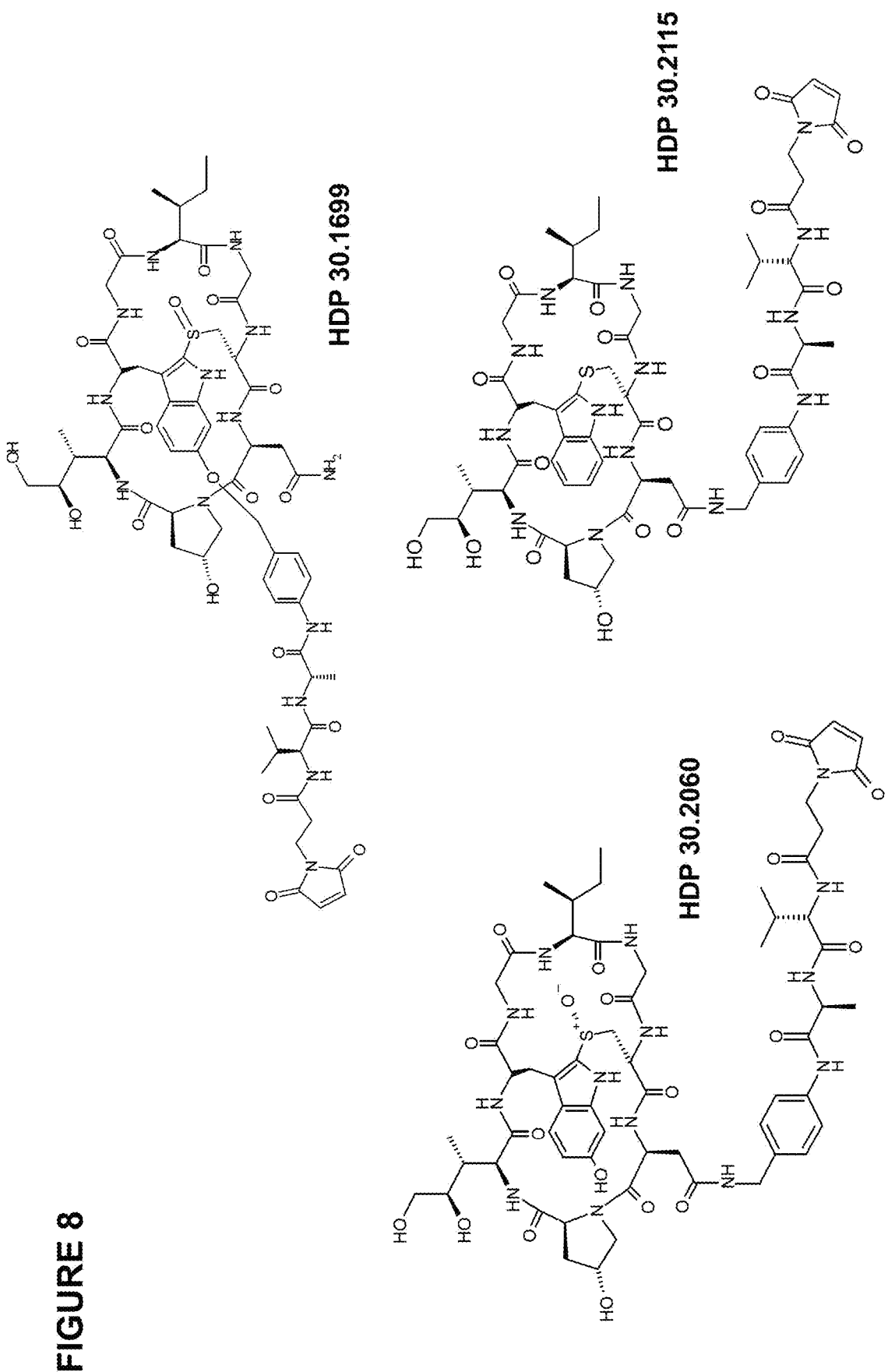
FIG. 8 shows alpha-amanitin derivative HDP 30.1699 with cleavable linker at AA4-6-OH moiety, beta-amanitin derivative HDP 30.2060 with cleavable linker at AA1 γ-position and double deoxy amatoxin variant HDP 30.2115 with cleavable linker at AA1 γ-position.
Figure 9:
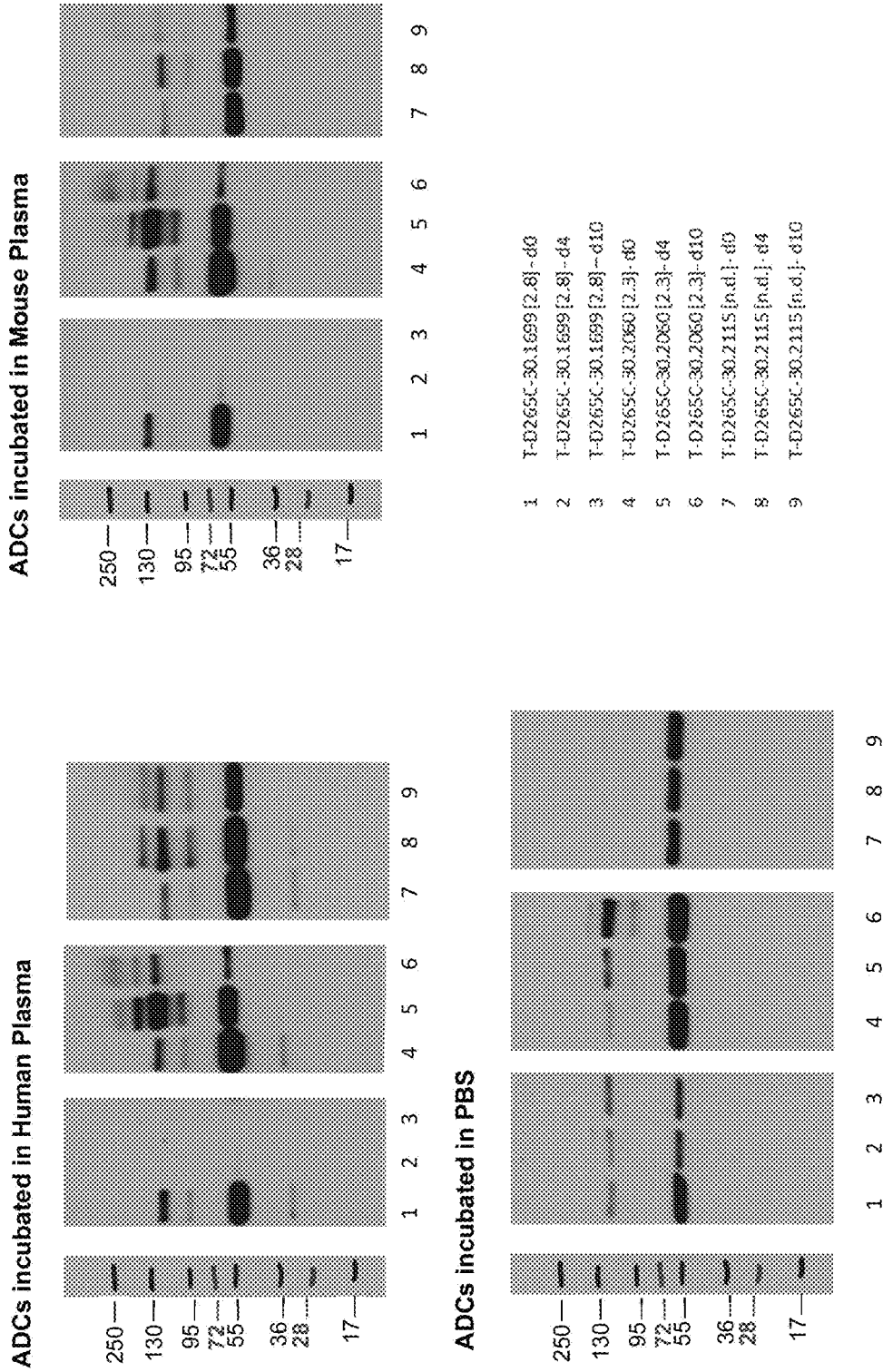
FIG. 9 shows. Western-Blot analysis of amatoxin derivatives HOP 30.1699, HDP 30.2060 and HDP 30.2115 conjugated to T-D265C antibody after incubation at 37° C. in human plasma, mouse plasma an phosphate buffered saline (PBS) for 0, 4 and 10 days. Detection was done with a polyclonal anti-amanitin antibody from rabbit and an anti-rabbit antibody conjugated to horseradish peroxidase. HDP 30.1699 and HOP 30.2060 showed considerable cross-links and loss of the amatoxin moiety. Double deoxy amanitin variant HDP 30.2115 shows high stability and significantly reduced cross-links.
Figure 10:
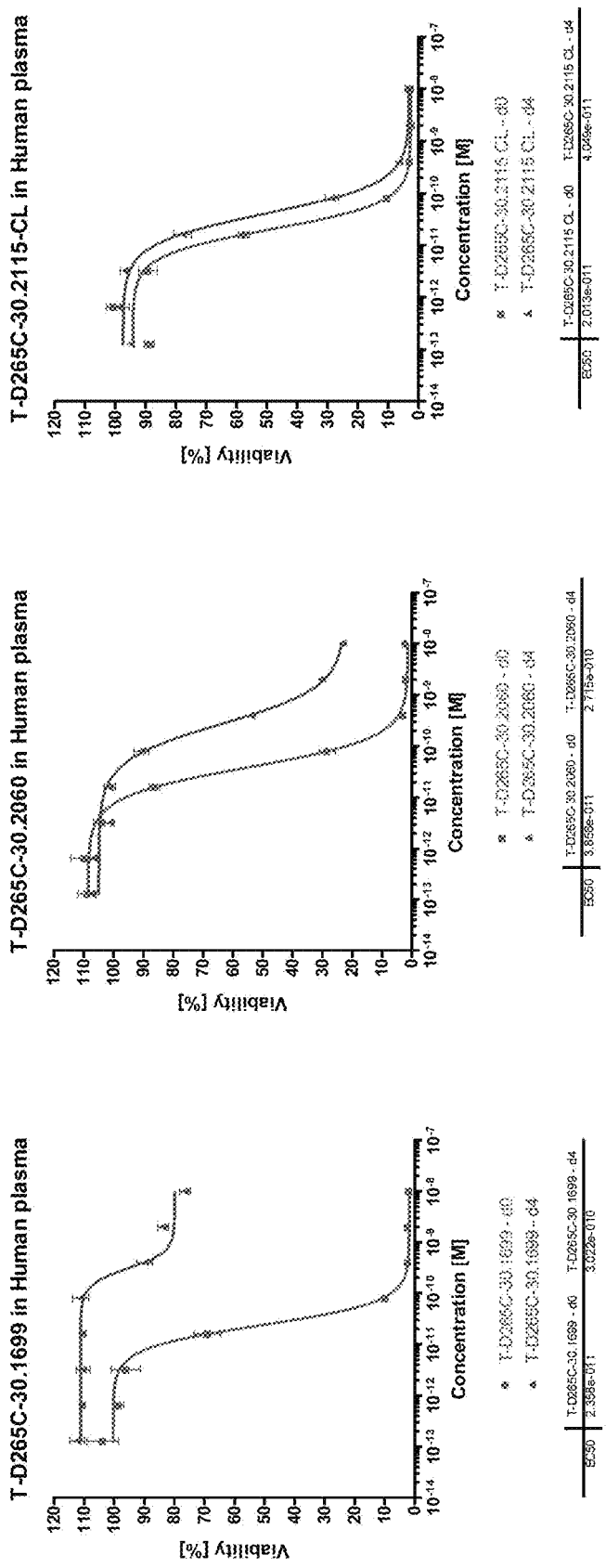
FIG. 10 shows cytotoxicity of amatoxin derivatives HDP 30.1699, HOP 30.2060 and HDP 30.2115 conjugated to T-D265C antibody. Test items were incubated in human plasma at 37° C. for 0 an 4 days. Cytotoxicity assay were performed on SKBR-3 cells for 96 h. HDP 30.1699 and HDP 30.2060 based ADCs show remarkable loss of cytotoxicity after 4 days plasma stressing whereas deoxygenated derivative HDP 30.2115 shows still picomolar activity
Figure 11:
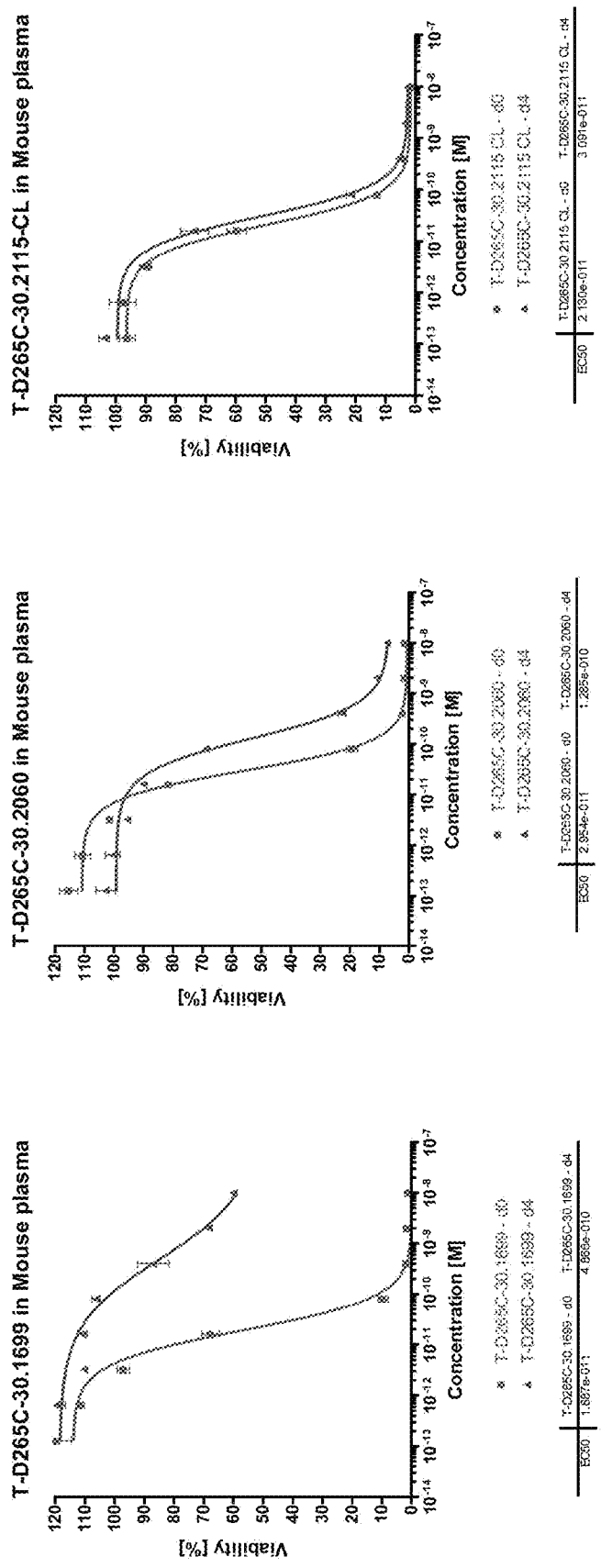
FIG. 11 shows cytotoxicity of amatoxin derivatives HDP 30.1699, HDP 30.2060 and HDP 30.2115 conjugated to T-D265C antibody. Test items were incubated in mouse plasma at 37° C. for 0 an 4 days. Cytotoxicity assay were performed on SKBR-3 cells for 96 h. HDP 30.1699 and HDP 30.2060 based ADCs show remarkable loss of cytotoxicity after plasma stressing whereas deoxygenated derivative HOP 30.2115 remains almost unchanged.
Figure 12:
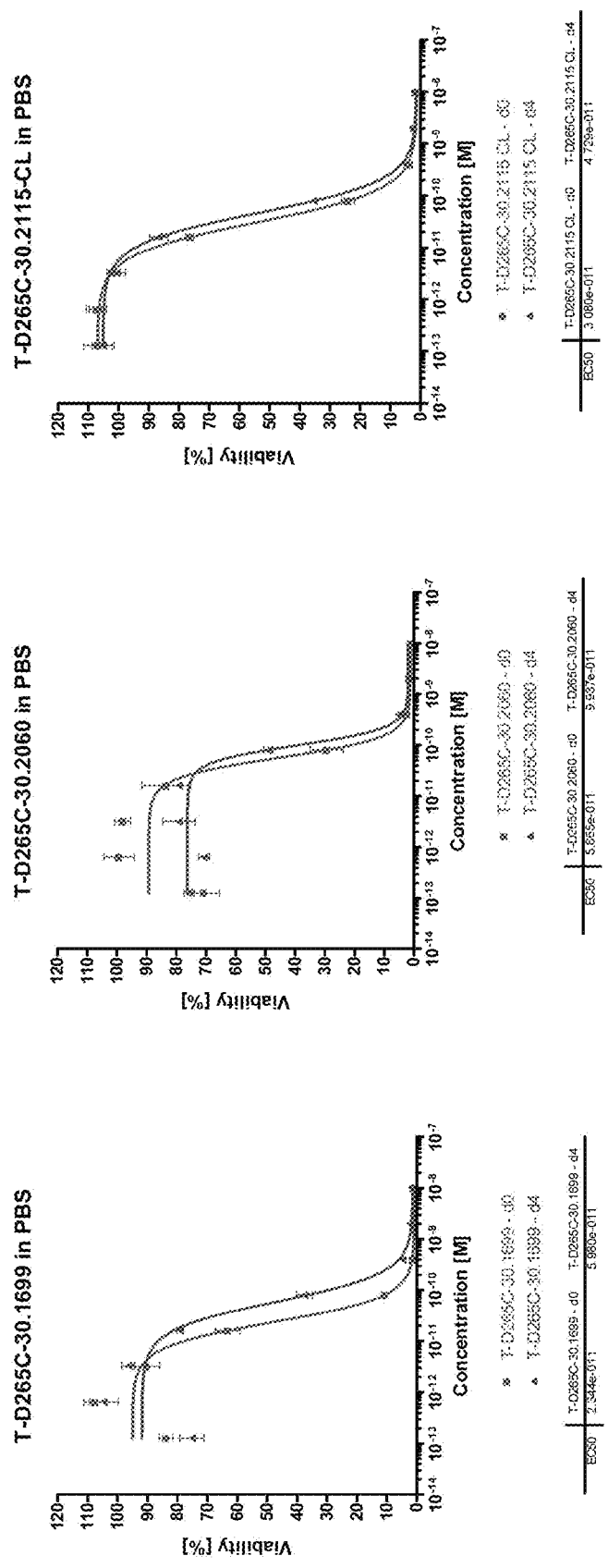
FIG. 12 shows cytotoxicity of amatoxin derivatives HDP 30.1699, HDP 30.2060 and HOP 30.2115 conjugated to T-D265C antibody. Test items were incubated in PBS at 37° C. for 0 an 4 days. Cytotoxicity assay were performed on SKBR-3 cells for 96 h. All ADCs show adequate stability to non-enzymatic environment.
Figure 13:
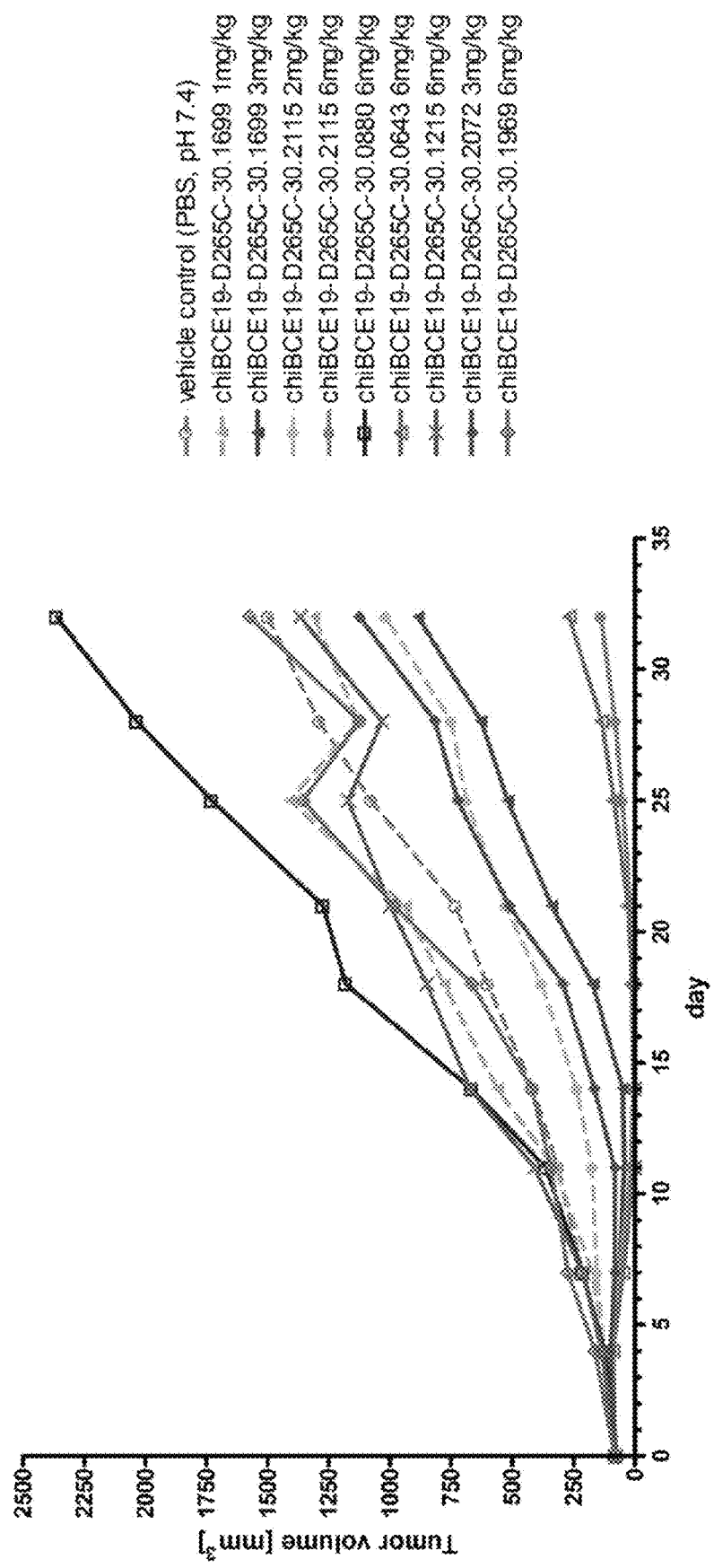
FIG. 13 compares the antitumoral activity of different chiBCE19-D265C antibody-amatoxin conjugates in Raji s.c. xenograft model-single dose experiment. Depending on linker and toxin structure significant differences in antitumoral activity have been observed. The deoxy-amanin variant chiBCE19-30.2115 (6"-deoxy at amino acid 4 and S-deoxy at amino acid 8) showed best antitumoral activity of all amatoxin ADCs, with a significantly better therapeutic index than corresponding cleavable linker ADC chiBCE19-30.1699 (lysine conjugation via 6'-OH; S=O at amino acid 8).
Figure 14:
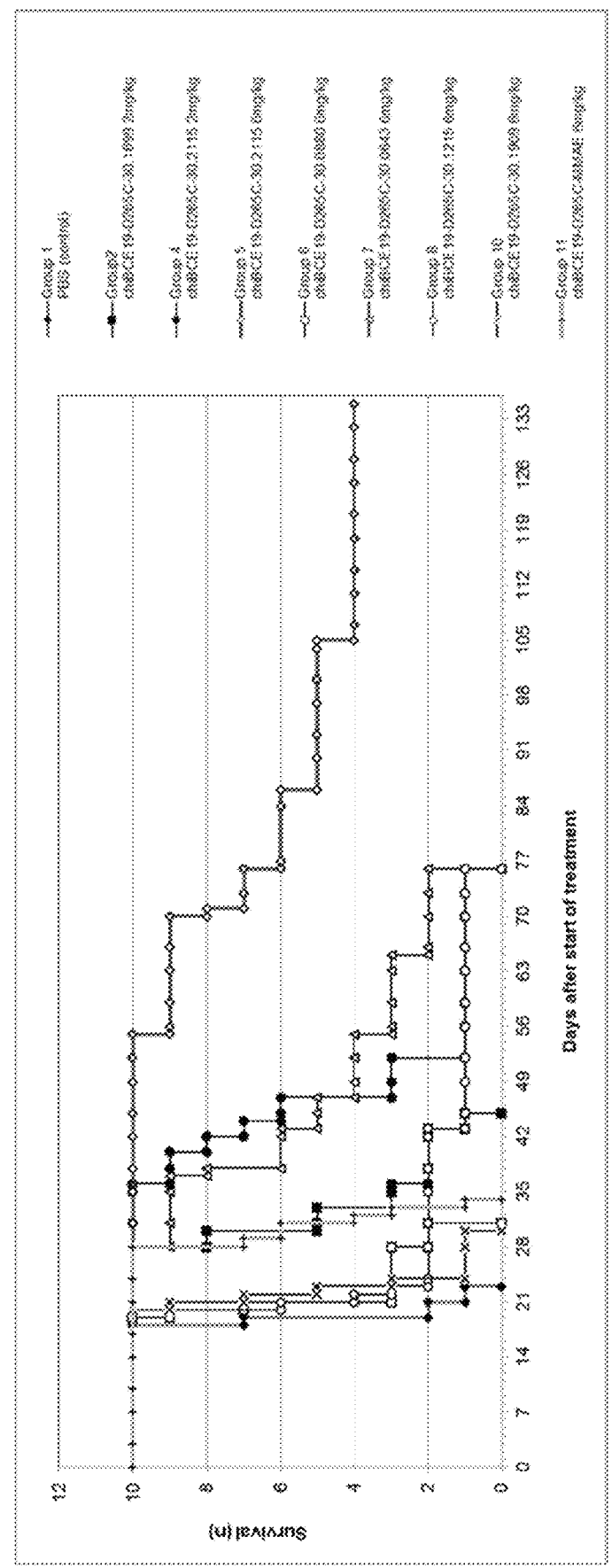
FIG. 14 shows the Kaplan Meier survival analysis in a systemic Raji tumor model-single dose experiment. In brief, $2.5 \times 10^6$ Raji (human Burkitt's lymphoma) tumour cells in 200 μL PBS/mouse were inoculated intravenously on day 0. Therapy (single dose, iv) was initiated on day 3 post tumor cell inoculation. The deoxy-amanin variant chiBCE19-30.2115 (6'-deoxy at amino acid 4 and S-deoxy at amino acid 8) showed superior survival over α-amanitin derivatives HDP 30.1699, HDP 30.0880 and HDP 30.0643 as well as the corresponding MMAE-derivative.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Particularly, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. In such latter embodiments, the term "comprising" is used coterminous with "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law. Nothing herein is to be construed as an admission that the invention is not entitled to antedate such disclosure by virtue of prior invention.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present invention is based on the unexpected observation that a variant form of amatoxins with (i) an amino acid 4 with a 6'-deoxy position; and (ii) an amino acid 8 with an S-deoxy position, shows an increased stability under stress conditions and an improved therapeutic index.

Thus, in one aspect the present invention relates to a conjugate comprising (a) an amatoxin comprising (i) an amino acid 4 with a 6'-deoxy position; and (ii) an amino acid 8 with an S-deoxy position; (b) a target-binding moiety; and (c) optionally a linker linking said amatoxin and said target-binding moiety. In particular, the optional linker of (c) is present and is a cleavable linker.

Zhao et al., ChemBioChem 16 (2015) 1420-1425, reported the synthesis of such a di-deoxy amatoxin core. However, the method of Zhao et al. resulted in a mixture of four different diastereomers, with only one of them exhibiting the desired toxicity of the natural products. Thus, as fully correctly identified by Zhao et al., the production of the single toxic diastereomer in pure form still represented a key need (Zhao et al. loc. cit., p. 1424, left column). While Zhao et al. proposed a lengthy list of potential routes to achieve such result, the proposals given are not more than an invitation to perform research. Additionally, while Zhao et al. could confirm that the synthetic variant essentially maintains the toxicity of the corresponding natural product, the do not show any advantages of their new compound, and in particular do not provide any teaching or even any suggestion that amatoxin derivatives with a di-deoxy core in accordance with the present invention show an increased stability under stress conditions in plasma and do not result in cross-linked products. Thus, Zhao et al. do not provide any particular incentive for one of ordinary skill in the art to undertake the required efforts for such research activities.

In a particular embodiment, the present invention relates to a conjugate having structure I wherein:
$R^2$ is S;
$R^3$ is selected from $-NHR^5$, $-NH-OR^5$, and $-OR^5$,
$R^4$ is H; and
wherein one of $R^5$ is $-L_n-X$, wherein L is a linker, particularly a cleavable linker,
n is selected from 0 and 1, and X is a target-binding moiety, and wherein the remaining $R^5$ are H.

In the context of the present invention, the term "amatoxin" includes all cyclic peptides composed of 8 amino acids as isolated from the genus *Amanita* and described in Wieland, T. and Faulstich H. (Wieland T, Faulstich H., CRC Crit Rev Biochem. 5 (1978) 185-260), which comprise the specific positions according to (i) (i.e. where the indole moiety of the amino acid residue tryptophan has no oxygen-containing substituent at position 6', particularly where position 6' carries a hydrogen atom) and (ii) (i.e. in which the thioether sulfoxide moiety of naturally occurring amatoxins is replaced by a sulfide), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in each case wherein any such derivative or analogue carries at least the positions (i) and (ii) mentioned above and is functionally active by inhibiting mammalian RNA polymerase II.

Functionally, amatoxins are defined as peptides or depsipeptides that inhibit mammalian RNA polymerase II. Preferred amatoxins are those with a functional group (e.g. a carboxylic group or carboxylic acid derivative such as a carboxamide or hydroxamic acid, an amino group, a hydroxy group, a thiol or a thiol-capturing group) that can be reacted with linker molecules or target-binding moieties as defined above. Amatoxins which are particularly suitable for the conjugates of the present invention are di-deoxy variants of α-amanitin, δ-amanitin, γ-amanitin, ε-amanitin, amanullin, or amanullinic acid, or mono-deoxy variants of amanin, amaninamide, γ-amanin, or γ-amaninamide as shown in FIG. 1 as well as salts, chemical derivatives, semisynthetic analogues, and synthetic analogues thereof.

In a particular embodiment, the conjugate of the present invention has a purity greater than 90%, particularly greater than 95%.

In the context of the present invention, the term "purity" refers to the total amount of conjugates being present. A purity of greater than 90%, for example, means that in 1 mg of a composition comprising a conjugate of the present invention, there are more than 90%, i.e. more than 900 µg, of such conjugate. The remaining part, i.e. the impurities may include unreacted starting material and other reactants, solvents, cleavage products and/or side products.

In a particular embodiment, a composition comprising a conjugate of the present invention comprises more than 100 mg, in particular more than 500 mg, and more particularly more than 1 g of such conjugate. Thus, trace amount of a conjugate of the present invention that arguably may be present in complex preparations of conjugates of the prior art, e.g. from partial reduction of naturally occurring sulfoxides, are explicitly excluded.

The term "target-binding moiety", as used herein, refers to any molecule or part of a molecule that can specifically bind to a target molecule or target epitope. Preferred target-binding moieties in the context of the present application are (i) antibodies or antigen-binding fragments thereof; (ii) antibody-like proteins; and (iii) nucleic acid aptamers. "Target-binding moieties" suitable for use in the present invention typically have a molecular mass of 40000 Da (40 kDa) or more.

As used herein, a first compound (e.g. an antibody) is considered to "specifically bind" to a second compound (e.g. an antigen, such as a target protein), if it has a dissociation constant $K_D$ to said second compound of 100 µM or less, particularly 50 µM or less, particularly 30 µM or less, particularly 20 µM or less, particularly 10 µM or less, particularly 5 µM or less, more particularly 1 µM or less, more particularly 900 nM or less, more particularly 800 nM or less, more particularly 700 nM or less, more particularly 600 nM or less, more particularly 500 nM or less, more particularly 400 nM or less, more particularly 300 nM or less, more particularly 200 nM or less, even more particularly 100 nM or less, even more particularly 90 nM or less, even more particularly 80 nM or less, even more particularly 70 nM or less, even more particularly 60 nM or less, even more particularly 50 nM or less, even more particularly 40 nM or less, even more particularly 30 nM or less, even more particularly 20 nM or less, and even more particularly 10 nM or less.

In the context of the present application the terms "target molecule" and "target epitope", respectively, refers to an antigen and an epitope of an antigen, respectively, that is specifically bound by a target-binding moiety. Particularly the target molecule is a tumour-associated antigen, in particular an antigen or an epitope which is present on the surface of one or more tumour cell types in an increased concentration and/or in a different steric configuration as compared to the surface of non-tumour cells. Particularly, said antigen or epitope is present on the surface of one or more tumour cell types, but not on the surface of non-tumour cells. In particular embodiments, the target-binding moiety specifically binds to an epitope of an antigen selected from: PSMA, CD19, CD269, sialyl Lewis$^a$, HER-2/neu and epithelial cell adhesion molecule (EpCAM). In other embodiments, said antigen or epitope is preferentially expressed on cells involved in autoimmune diseases. In particular such embodiments, the target-binding moiety specifically binds to an epitope of the IL-6 receptor (IL-6R).

The term "antibody or antigen binding fragment thereof", as used herein, refers to immunoglobulin molecules and immunologically active portions of immunoglobulin molecules, i.e. molecules that contain an antigen-binding site that immunospecifically binds an antigen. Thus, the term "antigen-binding fragments thereof" refers to a fragment of an antibody comprising at least a functional antigen-binding domain. Also comprised are immunoglobulin-like proteins that are selected through techniques including, for example, phage display to specifically bind to a target molecule, e.g. to a target protein selected from: PSMA, CD19, CD269, sialyl Lewis$^a$, Her-2/neu and EpCAM. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. "Antibodies and antigen-binding fragments thereof" suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, F(ab')$_2$ fragments, fragments produced by a Fab expression library, diabodies or tetrabodies (Holliger P. et al., Proc Natl Acad Sci USA. 90 (1993) 6444-8), nanobodies, anti-idiotypic (anti-Id) antibodies (including, e.g., anti-Id antibodies to antibodies of the invention), and epitope-binding fragments of any of the above.

In some embodiments the antigen-binding fragments are human antigen-binding antibody fragments of the present invention and include, but are not limited to, Fab, Fab' and F(ab')2, Fd, single-chain Fvs (scFv), single-chain antibodies, disulfide-linked Fvs (dsFv) and fragments comprising either a VL or VH domain. Antigen-binding antibody fragments, including single-chain antibodies, may comprise the variable domain(s) alone or in combination with the entirety or a portion of the following: hinge region, CL, CH1, CH2, and CH3 domains. Also included in the invention are antigen-binding fragments also comprising any combination of variable domain(s) with a hinge region, CL, CH1, CH2, and CH3 domains.

Antibodies usable in the invention may be from any animal origin including birds and mammals. Particularly, the antibodies are from human, rodent (e.g. mouse, rat, guinea pig, or rabbit), chicken, pig, sheep, goat, camel, cow, horse, donkey, cat, or dog origin. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Particularly, the scaffold protein is a small globular protein. Antibody-like proteins include without limitation affibodies, anticalins, and designed ankyrin repeat proteins (for review see: Binz et al., Nat Biotechnol. 2005, 1257-68). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins.

The term "nucleic acid aptamer" refers to a nucleic acid molecule that has been engineered through repeated rounds of in vitro selection or SELEX (systematic evolution of ligands by exponential enrichment) to bind to a target molecule (for a review see: Brody and Gold, J Biotechnol. 74 (2000) 5-13). The nucleic acid aptamer may be a DNA or RNA molecule. The aptamers may contain modifications, e.g. modified nucleotides such as 2'-fluorine-substituted pyrimidines.

A "linker" in the context of the present invention refers to a structure that is connecting two components, each being attached to one end of the linker. In the case of the linker being a bond, a direct linkage of amatoxin to the antibody may decrease the ability of the amatoxin to interact with RNA polymerase II. In particular embodiments, the linker increases the distance between two components and alleviates steric interference between these components, such as in the present case between the antibody and the amatoxin. In particular embodiments, the linker has a continuous chain of between 1 and 30 atoms (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 atoms) in its backbone, i.e. the length of the linker is defined as the shortest connection as measured by the number of atoms or bonds between the amatoxin moiety and the antibody, wherein one side of the linker backbone has been reacted with the amatoxin and, the other side is available for reaction, or has been reacted, with an antibody. In the context of the present invention, a linker particularly is a $C_{1-20}$-alkylene, $C_{1-20}$-heteroalkylene, $C_{2-20}$-alkenylene, $C_{2-20}$-heteroalkenylene, $C_{2-20}$-alkynylene, $C_{2-20}$-heteroalkynylene, cycloalkylene, heterocycloalkylene, arylene, heteroarylene, aralkylene, or a heteroaralkylene group, optionally substituted. The linker may contain one or more structural elements such as carboxamide, ester, ether, thioether, disulfide, urea, thiourea, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the amatoxin and the antibody. To that end the linker to be will carry two groups, particularly at a proximal and distal end, which can (i) form a covalent bond to a group present in one of the components to be linked, particularly an activated group on an amatoxin or the target binding-peptide or (ii) which is or can be activated to form a covalent bond with a group on an amatoxin. Accordingly, it is preferred that chemical groups are at the distal and proximal end of the linker, which are the result of such a coupling reaction, e.g. an ester, an ether, a urethane, a peptide bond etc.

In particular embodiments, the linker L is a linear chain of between 1 and 20 atoms independently selected from C, O, N and S, particularly between 2 and 18 atoms, more particularly between 5 and 16 atoms, and even more particularly between 6 and 15 atoms. In particular embodiments, at least 60% of the atoms in the linear chain are C atoms. In particular embodiments, the atoms in the linear chain are linked by single bonds.

In particular embodiments. the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted.

The term "alkylene" refers to a bivalent straight chain saturated hydrocarbon groups having from 1 to 20 carbon atoms, including groups having from 1 to 10 carbon atoms. In certain embodiments, alkylene groups may be lower alkylene groups. The term "lower alkylene" refers to alkylene groups having from 1 to 6 carbon atoms, and in certain embodiments from 1 to 5 or 1 to 4 carbon atoms. Examples of alkylene groups include, but are not limited to, methylene ($-CH_2-$), ethylene ($-CH_2-CH_2-$), n-propylene, n-butylene, n-pentylene, and n-hexylene.

The term "alkenylene" refers to bivalent straight chain groups having 2 to 20 carbon atoms, wherein at least one of the carbon-carbon bonds is a double bond, while other bonds may be single bonds or further double bonds. The term "alkynylene" herein refers to groups having 2 to 20 carbon atoms, wherein at least one of the carbon-carbon bonds is a triple bond, while other bonds may be single, double or further triple bonds. Examples of alkenylene groups include ethenylene ($-CH=CH-$), 1-propenylene, 2-propenylene, 1-butenylene, 2-butenylene, 3-butenylene, and the like. Examples of alkynylene groups include ethynylene, 1-propynylene, 2-propynylene, and so forth.

As used herein, "cycloalkylene" is intended to refer to a bivalent ring being part of any stable monocyclic or polycyclic system, where such ring has between 3 and 12 carbon atoms, but no heteroatom, and where such ring is fully saturated, and the term "cycloalkenylene" is intended to refer to a bivalent ring being part of any stable monocyclic or polycyclic system, where such ring has between 3 and 12 carbon atoms, but no heteroatom, and where such ring is at least partially unsaturated (but excluding any arylene ring). Examples of cycloalkylenes include, but are not limited to, cyclopropylene, cyclobutylene, cyclopentylene, cyclohexylene, and cycloheptylene. Examples of cycloalkenylenes include, but are not limited to, cyclopentenylene and cyclohexenylene.

As used herein, the terms "heterocycloalkylene" and "heterocycloalkenylene" are intended to refer to a bivalent ring being part of any stable monocyclic or polycyclic ring system, where such ring has between 3 and about 12 atoms, and where such ring consists of carbon atoms and at least one heteroatom, particularly at least one heteroatom independently selected from the group consisting of N, O and S, with heterocycloalkylene referring to such a ring that is fully saturated, and heterocycloalkenylene referring to a ring that is at least partially unsaturated (but excluding any arylene or heteroarylene ring).

The term "arylene" is intended to mean a bivalent ring or ring system being part of any stable monocyclic or polycyclic system, where such ring or ring system has between 3 and 20 carbon atoms, but has no heteroatom, which ring or ring system consists of an aromatic moiety as defined by the "4n+2" π electron rule, including phenylene.

As used herein, the term "heteroarylene" refers to a bivalent ring or ring system being part of any stable mono- or polycyclic system, where such ring or ring system has between 3 and 20 atoms, which ring or ring system consists of an aromatic moiety as defined by the "4n+2" π electron rule and contains carbon atoms and one or more nitrogen, sulfur, and/or oxygen heteroatoms.

In the context of the present invention, the term "substituted" is intended to indicate that one or more hydrogens present in the backbone of a linker is replaced with a selection from the indicated group(s), provided that the indicated atom's normal valency, or that of the appropriate atom of the group that is substituted, is not exceeded, and that the substitution results in a stable compound. The term "optionally substituted" is intended to mean that the linker is either unsubstituted or substituted, as defined herein, with one or more substituents, as defined herein. When a substituent is a keto (or oxo, i.e. =O) group, a thio or imino group or the like, then two hydrogens on the linker backbone atom are replaced. Exemplary substituents include, for example, alkyl, alkenyl, alkynyl, cycloalkyl, heterocycloalkyl, aryl, heteroaryl, aralkyl, heteroaralkyl, acyl, aroyl, heteroaroyl, carboxyl, alkoxy, aryloxy, acyloxy, aroyloxy, heteroaroyloxy, alkoxycarbonyl, halogen, (thio)ester, cyano, phosphoryl, amino, imino, (thio)amido, sulfhydryl, alkylthio, acylthio, sulfonyl, a sulfate, a sulfonate, a sulfamoyl, a sulfonamido, nitro, azido, haloalkyl, including perfluoroalkyl (such as trifluoromethyl), haloalkoxy, alkylsulfanyl, alkylsulfinyl, alkylsulfonyl, alkylsulfonylamino, arylsulfonoamino, phosphoryl, phosphate, phosphonate, phosphinate, alkylcarboxy, alkylcarboxyamide, oxo, hydroxy, mercapto, amino (optionally mono- or di-substituted, e.g. by alkyl, aryl, or heteroaryl), imino, carboxamide, carbamoyl (optionally mono- or di-substituted, e.g. by alkyl, aryl, or heteroaryl), amidino, aminosulfonyl, acylamino, aroylamino, (thio)ureido, (arylthio)ureido, alkyl(thio)ureido, cycloalkyl(thio)ureido, aryloxy, aralkoxy, or —O(CH$_2$)$_n$—OH, —O(CH$_2$)$_n$—NH$_2$, —O(CH$_2$)$_n$COOH, —(CH$_2$)$_n$COOH, —C(O)O(CH$_2$)$_n$R, —(CH$_2$)$_n$N(H)C(O)OR, or —N(R)S(O)$_2$R wherein n is 1-4 and R is independently selected from hydrogen, -alkyl, -alkenyl, -alkynyl, -cycloalkyl, -cycloalkenyl, —(C-linked-heterocycloalkyl), —(C-linked-heterocycloalkenyl), -aryl, and -heteroaryl, with multiple degrees of substitution being allowed. It will be understood by those skilled in the art that substituents, such as heterocycloalkyl, aryl, heteroaryl, alkyl, etc., or functional groups such as —OH, —NHR etc., can themselves be substituted, if appropriate. It will also be understood by those skilled in the art that the substituted moieties themselves can be substituted as well when appropriate.

In particular embodiments, the linker L comprises a moiety selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—).

In particular embodiments of the present invention, the linker L comprises a number of m groups selected from the list of: alkylene, alkenylene, alkynylene, cycloalkylene, heteroalkylene, heteroalkenylene, heteroalkynylene, heterocycloalkylene, arylene, heteroarylene, aralkylene, and a heteroaralkylene group, wherein each group may optionally be independently substituted, the linker further comprises a number of n moieties independently selected from one of the following moieties: a disulfide (—S—S—), an ether (—O—), a thioether (—S—) an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—), wherein m=n+1. In particular embodiments, m is 2 and n is 1, or m is 3 and n is 2. In particular embodiments, the linker comprises 2 or 3 unsubstituted alkylene groups, and 1 or 2, respectively, disulfide, ether, thioether, amine, ester, carboxamide, urethane or urea moieties linking the unsubstituted alkylene groups.

In a particular embodiment, the linker L does not comprise a heteroarylene group.

In particular embodiments, the C atoms in the linear chain are independently part of optionally substituted methylene groups (—CH$_2$—). In particular such embodiments, the optional substituents are independently selected from halogen and C$_{1-6}$-alkyl, particularly methyl.

In particular embodiments, the linker L is a stable linker.

In the context of the present invention, the term "stable linker" refers to a linker that is stable (i) in the presence of enzymes, and (ii) in an intracellular reducing environment.

In particular embodiments, the stable linker does not contain (i) an enzyme-cleavable substructure, and/or (ii) a disulfide group. In particular such embodiments, the linker has a length of up to 12 atoms, particularly from 2 to 10, more particularly from 4 to 9, and most particularly from 6 to 8 atoms.

In particular other embodiments, the linker is a cleavable linker.

In the context of the present invention, the term "cleavable linker" refers to a linker that is (i) cleavable by an enzyme, or (ii) a reducible linker. In particular embodiments, the term only refers to a linker that is cleavable by an enzyme (not to a reducible linker).

In the context of the present invention, the term "linker that is cleavable . . . by an enzyme" refers to a linker that can be cleaved by an enzyme, particularly by a lysosomal peptidase, such as Cathepsin B, resulting in the intracellular release of the toxin cargo conjugated to the targeting antibody after internalization (see Dubowchik et al., Bioconjug Chem. 13 (2002) 855-69). In particular embodiments, the cleavable linker comprises a dipeptide selected from: Phe-Lys, Val-Lys, Phe-Ala, Val-Ala, Phe-Cit and Val-Cit, particularly wherein the cleavable linker further comprises a p-aminobenzyl (PAB) spacer between the dipeptides and the amatoxin.

In particular such embodiments, the cleavable linker comprises a structure L$_1$-L*-L$^2$

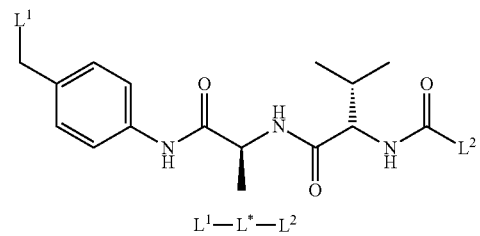

L$^1$—L*—L$^2$ wherein L$^1$ is a part of the linker that connects L* to the amatoxin, in particular, wherein L$^1$ is connected to L* via a —NH— or a —O— group, particularly a —C(=O)—NH—, a —C(=O)—NH—O— or a —C(=O)—O— group, and wherein L$^2$ is a part of the linker that connects L* to the target-binding moiety, in particularly wherein L$^1$ is connected to L* via a —(CH$_2$)$_m$— moiety, with m being an integer selected from 1 to 8, in particular from 1 to 5, or via a —(CH$_2$CH$_2$O)$_n$— moiety, with n being an integer selected from 1 to 3, in particular from 1 to 2.

In particular other such embodiments, L* has the following structure

In particular embodiments, the linker $L^1$ is a linear chain of between 1 and 4 atoms independently selected from C, O, N and S, particularly between 1 and 3 atoms, more particularly between 1 and 2 atoms, and even more just 1 atom. In particular embodiments, at least 50% of the atoms in the linear chain are C atoms. In particular embodiments, the atoms in the linear chain are linked by single bonds.

In the context of the present invention, the term "reducible linker" refers to a linker that can be cleaved in the intracellular reducing environment, particularly a linker that contains a disulfide groups, resulting in the intracellular release of the toxin cargo conjugated to the target-binding moiety after internalization by the intracellular reducing environment (see Shen et al., J. Biol. Chem. 260 (1985) 10905-10908). In particular embodiments, the reducible linker comprises a moiety wherein R1 to R4 are independently selected from H and methyl.

In particular such embodiments, such cleavable linker has a length of up to 20 atoms, particularly from 6 to 18, more particularly from 8 to 16, and most particularly from 10 to 15 atoms. In particular such embodiments, the part of the linker linking the amatoxin according to the present invention and the cleavable disulfide group is a linear chain of 3 or 4 C atoms, particularly 3 C atoms. In particular embodiments, the 3 or 4 C atoms in the linear chain are linked by single bonds. In particular embodiments, the linker is an n-propylene group.

In particular embodiments, said linker is present and is connected on one side to a position in the amatoxin of formula I selected from
  (i) in the case of a conjugate of formula I with $R^3$=NHR$^5$, the nitrogen atom of the amide group at the γ C-atom of amatoxin amino acid 1 (amide linkage);
  (ii) in the case of a conjugate of formula I with $R^3$=OR$^5$, the oxygen atom of the acid group at the γ C-atom of amatoxin amino acid 1 (ester linkage);
  (iii) in the case of a conjugate of formula I with $R^3$=NHOR$^5$, the oxygen atom of the hydroxamic acid group at the γ C-atom of amatoxin amino acid 1;
  (iv) the oxygen atom of the hydroxy group at the δ C-atom of amatoxin amino acid 3, particularly via an ester linkage, an ether linkage or a urethane linkage; or
  (v) the ring nitrogen of amino acid 4.

In particular such embodiments, said linker is present and is connected on one side to a position in the amatoxin of formula I selected from (ii) to (v) shown above. In particular embodiments, said linker is present and is connected on one side to a position in the amatoxin of formula I selected from (iv) to (v) shown above.

Coupling of the linker to the target-binding moiety can be achieved by a variety of methods well known to one of ordinary skill in the art, particularly in the art of antibody-drug conjugates (ADCs).

In particular embodiments, said linker is connected to the target-binding moiety via a urea moiety ( . . . -linker-NH—C(=O)—NH-target-binding moiety). In particular such embodiments, the urea moiety results from a reaction of a primary amine originally present in the target-binding moiety, such as an amino group of a lysine side chain, with a carbamic acid derivative . . . -linker-NH—C(O)—Z, wherein Z is a leaving group that can be replaced by a primary amine.

In particular other embodiments, said linker is present and is connected to the target-binding moiety via a thioether moiety ( . . . -linker-S-target-binding moiety). Thus, in such embodiments, the present invention relates to a conjugate of generic formula:

Dideoxyxamatoxin-L-X*-S-Tbm, wherein Dideoxyxamatoxin is an amatoxin according to the present invention, L is a linker, X* is a moiety resulting from coupling of a thiol group to a thiol-reactive group, S is the sulphur atom of said thiol group, particularly the thiol group of a cysteine amino acid residue, and Tbm is a target-binding moiety, particularly an antibody or a functional antibody fragment comprising said cysteine amino acid residue. In particular embodiments, said cysteine amino acid residue (i) is located in an antibody domain selected from CL, CH1, CH2, and CH3; (ii) is located at a position, where the germline sequence exhibiting the closest homology to the sequence of said antibody domain contains an amino acid residue different from cysteine; and (iii) is located a position that is solvent-exposed.

In the context of the present invention, the term "thiol-reactive group" refers to a group that selectively reacts with the thiol group of, for example, a free cysteine of an antibody, particularly in a pH value in the range between 6.0 and 8.0, more particularly in a pH value in the range between 6.5 and 7.5. In particular, the term "selectively" means that less than 10% of the coupling reactions of a molecule comprising a thiol-reactive group with an antibody comprising at least one free cysteine residue are coupling reactions with non-cysteine residues of the antibody, such as lysine residues, particularly less than 5%, more particularly less than 2%. In particular embodiments, the thiol-reactive group is selected from bromoacetamide, iodoacetamide, maleimide, a maleimide having a leaving group in position 3, in particular a leaving group selected from —Br, and substituted thiol (see, for example, U.S. Pat. No. 9,295,729), a 1,2-dihydropyridazine-3,6-dione having a leaving group in position 4, in particular a leaving group selected from —Br, and substituted thiol (see, for example, U.S. Pat. No. 9,295,729), methylsulfonyl benzothiazole, methylsulfonyl phenyltetrazole, methylsulfonyl phenyloxadiazole (see Toda et al., Angew. Chem. Int. Ed. Engl., 52 (2013) 12592-6), a 3-arylpropionitrile (see Kolodych et al, Bioconjugate Chem. 2015, 26, 197-200), and 5-nitro-pyridin-2-yl-disulfide ( . . . -L-S-S-(5-nitro-pyridine-2-yl).

In particular embodiments, said position or functional group, which is on one side connected to the linker and which can directly or indirectly be connected to a position or functional group present in a target-binding moiety is a moiety that can react with two thiol groups present in one target-binding moiety or in two target-binding moieties. In particular embodiments, the thiol-reactive groups is a maleimide having two leaving groups in positions 3 and 4, in particular selected from 3,4-dibromomaleimide, 3,4-bis(arylthio)-maleimide, in particular 3,4-diphenylthio-maleimide, and 3,4-bis(heteroarylthio)-maleimide, in particular 3,4-bis(2-pyridinyl-sulfanyl)-maleimide, and. In particular other embodiments, the thiol-reactive groups is a 1,2-dihydropyridazine-3,6-dione having two leaving groups in positions 4 and 5, in particular selected from 4,5-bromo-1,2-dihydropyridazine-3,6-dione, 4,5-bis(arylthio)-1,2-dihydropyridazine-3,6-dione, in particular 4,5-diphenylthio-1,2-dihydropyridazine-3,6-dione, and 4,5-bis(heteroarylthio)-1,2-dihydropyridazine-3,6-dione, in particular 4,5-bis(2-pyridinyl-sulfanyl)-1,2-dihydropyridazine-3,6-dione.

In particular embodiments, the moiety resulting from coupling of a thiol group to a thiol-reactive group is selected from: thiol-substituted acetamide; thiol-substituted succinimide; thiol-substituted succinamic acid; thiol-substituted heteroaryl, particularly thiol-substituted benzothiazole, thiol-substituted phenyltetrazole and thiol-substituted phenyloxadiazole; and a disulphide, wherein one sulphur atom is derived from a cysteine residue of the antibody. In particular embodiments, the moiety resulting from coupling of a thiol group to a thiol-reactive group is a thiol-substituted succinimide.

In particular embodiments, the linker L in the moiety L-X*-S present in the generic formula of section [0070], is selected from the following group of moieties:

(dideoxyamatoxin side) —$(CH_2)_2$—S—S—$(CH_2)_2$—X—S— (Tbm side);
(dideoxyamatoxin side) —$(CH_2)_3$—S—S—$(CH_2)_2$—X—S— (Tbm side);
(dideoxyamatoxin side) —$(CH_2)_2$—S—S—$(CH_2)_3$—X—S— (Tbm side);
(dideoxyamatoxin side) —$(CH_2)_3$—S—S—$(CH_2)_3$—X—S— (Tbm side);
(dideoxyamatoxin side) —$(CH_2)_4$—S—S—$(CH_2)_4$—X—S— (Tbm side);
(dideoxyamatoxin side) —$(CH_2)_2$—$CMe_2$-S—S—$(CH_2)_2$—X—S— (Tbm side);
(dideoxyamatoxin side) —$(CH_2)_2$—S—S—$CMe_2$-$(CH_2)_2$—X—S— (Tbm side);
(dideoxyamatoxin side) —$(CH_2)_3$—S—S— (Tbm side);
(dideoxyamatoxin side) —$CH_2$—$C_6H_4$—NH-Cit-Val-CO$(CH_2)_6$—X—S— (Tbm side)
(dideoxyamatoxin side) —$CH_2$—$C_6H_4$—NH-Ala-Val-CO$(CH_2)_6$—X—S— (Tbm side);
(dideoxyamatoxin side) —$CH_2$—$C_6H_4$—NH-Ala-Val-CO$(CH_2)_2$—X—S— (Tbm side);
(dideoxyamatoxin side) —$CH_2$—$C_6H_4$—NH-Ala-Phe-CO$(CH_2)_2$—X—S— (Tbm side);
(dideoxyamatoxin side) —$CH_2$—$C_6H_4$—NH-Lys-Phe-CO$(CH_2)_2$—X—S— (Tbm side);
(dideoxyamatoxin side) —$CH_2$—$C_6H_4$—NH-Cit-Phe-CO$(CH_2)_2$—X—S— (Tbm side);
(dideoxyamatoxin side) —$CH_2$—$C_6H_4$—NH-Val-Val-CO$(CH_2)_2$—X—S— (Tbm side);
(dideoxyamatoxin side) —$CH_2$—$C_6H_4$—NH-Ile-Val-CO$(CH_2)_2$—X—S— (Tbm side);
(dideoxyamatoxin side) —$CH_2$—$C_6H_4$—NH-His-Val-CO$(CH_2)_2$—X—S— (Tbm side);
(dideoxyamatoxin side) —$CH_2$—$C_6H_4$—NH-Met-Val-CO$(CH_2)_2$—X—S— (Tbm side);
(dideoxyamatoxin side) —$CH_2$—$C_6H_4$—NH-Asn-Lys-CO$(CH_2)_2$—X—S— (Tbm side); and
wherein —NH— and —CO— flanking the dipeptide sequences represent amino and carbonyl moieties of the linker forming amide bonds to the carboxy- and the amino-terminus of the dipeptide, respectively.

In the context of the present invention, the term "a moiety resulting from coupling of a thiol group to a thiol-reactive group" refers to a structure that results from (i) the nucleophilic substitution of a leaving group Y present in a thiol-reactive group by the sulphur atom of a cysteine residue, for example a bromo acetamide group, a iodo acetamide, a 4,6-dichloro-1,3,5-triazin-2-ylamino group, an alkylsulfone or a heteroarylsulfone; (ii) the addition of the HS-group of a cysteine residue to an activated double bond of a thiol-reactive group, for example maleimide, or (iii) an disulfide exchange of an activated disulfide or methanethiosulfonate with the sulphur atom of a cysteine residue, for example with pyridine-2-thiol, 5-nitropyridine-2-thiol or methanesulfinate as leaving group; or (iv) any other chemical reaction that results in a stable bond between the sulphur atom of a cysteine residue and a reactive moiety being part of the thiol-reactive group.

The primary moiety resulting from coupling of thiol group may be optionally further derivatized, e.g. the succinimidyl thioether resulting from a maleimide can be hydrolysed to succinamic acid thioethers of the following generic structures In particular other embodiments, site-specific coupling can be achieved by reducing a disulfide bridge present in the target-binding moiety, and by reacting the two cysteine residues with a bridging moiety X* present in a Dideoxyxamatoxin L-X* construct (see Badescu et al. Bridging disulfides for stable and defined antibody drug conjugates. Bioconjugate Chemistry. 25 (2014) 1124-1136).

In a similar embodiment, site-specific coupling can be achieved by reducing a disulfide bridge present in the target-binding moiety, and by reacting the two cysteine residues with a bridging moiety X* present in a Dideoxyxamatoxin-L-X* construct, particularly wherein X* is (see Bryden et al., Bioconjug Chem, 25 (2014) 611-617; Schumacher et al., Org Biomol Chem, 2014, 7261-7269)

In a particular other embodiment, coupling is achieved by regiospecific coupling of an amino group present in the linker to a glutamine residue present in the target-binding moiety via a transaminase, particularly by coupling to glutamine Q295 of an antibody.

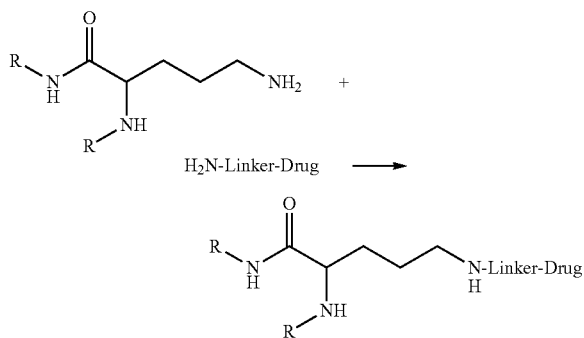

In a particular embodiment, coupling is achieved by site-specific conjugation to target-binding moieties comprising N-glycan side chains. In particular, the N-glycan side chain can be degraded enzymatically, followed by trans-glycosylation with an azido-galactose. Using click chemistry, such modified target-binding moiety can be coupled to appropriately modified constructs Dideoxyxamatoxin-L-X*, wherein X* is, for example, a dibenzo-cyclooctyne (DIBO) or an analogous moiety comprising a C—C triple bond. For example, a construct Dideoxyxamatoxin-L-$NH_2$ can be coupled to DIBO-SE

DIBO-SE 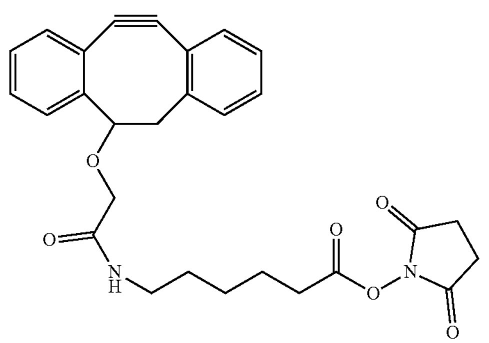 by nucleophilic substitution of the hydroxy succinimide moiety. The resulting DIBO-modified linker construct can then be coupled to the azido derivative mentioned above. In an alternative embodiment, the target-binding moiety can be modified by incorporation of a non-natural amino acid that permits click-chemistry, in particular by incorporation of a para-azidomethyl-L-phenylalanine (pAMF).

In particular embodiments, the linker L in -L-X* is a linear chain of at least 5, particularly at least 10, more particularly between 10 and 20 atoms independently selected from C, O, N and S, particularly between 10 and 18 atoms, more particularly between 10 and 16 atoms, and even more particularly between 10 and 15 atoms. In particular embodiments, at least 60% of the atoms in the linear chain are C atoms. In particular embodiments, the atoms in the linear chain are linked by single bonds.

In alternative embodiments, the position or functional group which can directly or indirectly be connected to a position or functional group present in a target-binding moiety, is not an ethynyl group, or, more generally, is not an alkynyl group, or is not a group that can be reacted with an 1,3 dipole in a 1,3-dipolar cycloaddition (click chemistry).

In particular other embodiments, site-specific coupling of a Dideoxyxamatoxin-L-X* construct to a target-binding moiety can be achieved by incorporation of a non-natural amino acid comprising a keto group, in particular p-acetylphenylalanine (pAcPhe), into the target-binding moiety, and by reacting such modified target-binding moiety with a Dideoxyxamatoxin-L-X* construct, wherein X* is a hydroxylamine moiety.

In a further embodiment, a formyl group can be introduced by formylglycine generating enzyme (FGE), which is highly selective for a cysteine group in a recognition sequence CxPxR to generate an aldehyde tag. Such aldehyde tag can be reacted with an appropriate group X* present in a Dideoxyxamatoxin-L-X* construct, in particular wherein X* is 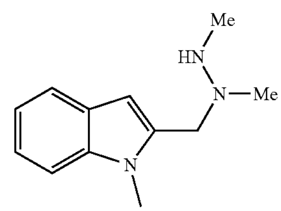 (see Agarwal et al., Bioconjugate Chem 24 (2013) 846-851).

In a second aspect, the present invention relates to a pharmaceutical composition comprising the conjugate of the present invention.

In a third aspect, the present invention relates to a conjugate of the present invention for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, leukemia, and malignant lymphoma.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the treatment may comprise administering a conjugate or a pharmaceutical composition according to the present invention to a patient, wherein "administering" includes in vivo administration, as well as administration directly to tissue ex vivo, such as vein grafts.

In particular embodiments, a therapeutically effective amount of the conjugate of the present invention is used.

A "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

In another aspect the present invention relates to pharmaceutical composition comprising an amatoxin according to the present invention, or a conjugate of the present invention of an amatoxin with a target-binding moiety, and further comprising one or more pharmaceutically acceptable diluents, carriers, excipients, fillers, binders, lubricants, glidants, disintegrants, adsorbents; and/or preservatives.

"Pharmaceutically acceptable" means approved by a regulatory agency of the Federal or a state government or listed in the U.S. Pharmacopeia or other generally recognized pharmacopeia for use in animals, and more particularly in humans.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the target-binding moiety toxin conjugates of the invention to proteins or polymers or they can also be added with the aim to reduce the adsorption of the target-binding moiety toxin conjugates of the invention to materials like injection instruments or packaging-materials, for example, plastic or glass.

The amatoxins of the present invention comprising a target-binding moiety can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the target-binding moiety toxin conjugates of the invention are introduced in finely dispersed, dispersed and suspended form, respectively, or as a suspension of crystals in the medicament or based on the "single unit principle" if the target-binding moiety toxin conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are particularly aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the target-binding moiety toxin conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrene, carboxymethyl cellulose, Pluronics® or polyethylene glycol sorbit fatty acid ester. The target-binding moiety toxin conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatine can be used.

In a fourth aspect, the present invention relates to a construct comprising (a) an amatoxin comprising (i) an amino acid 4 with a 6'-deoxy position; and (ii) an amino acid 8 with an S-deoxy position; and (c) a linker moiety carrying a reactive group for linking said amatoxin to a target-binding moiety.

In a particular embodiment, the present invention relates to a construct having structure II

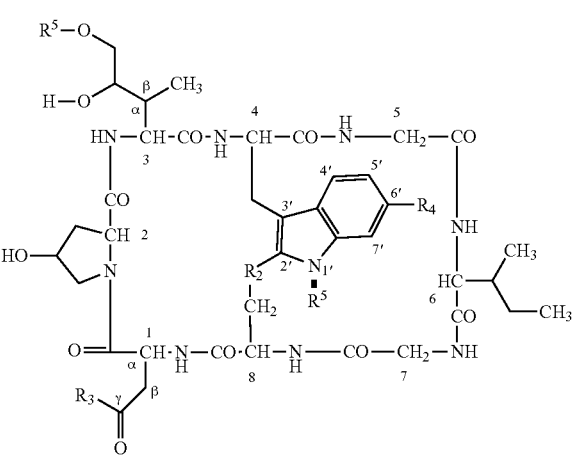

wherein:

R² is S;

R³ is selected from NHR⁵, —NH—OR⁵, and OR⁵;

R⁴ is H; and wherein one of R⁵ is -L-Y, wherein L is a linker, and Y is a reactive group for linking said construct to a target-binding moiety.

EXAMPLES

In the following, the invention is explained in more detail by non-limiting examples:

1. Synthesis of Synthetic Dideoxy Precursor Molecule K

The synthesis of the dideoxy precursor molecule K is described in WO 2014/009025 in Example 5.5.

K

Compound K may be deprotected by treatment with 7 N methanolic NH₃ solution (3.0 ml) and stirring overnight.

2. Synthesis of Synthetic Dideoxy Precursor HDP 30.2105

An alternative dideoxy precursor molecules comprising a —COOH group instead of the carboxamide group at amino acid 1 can be synthesized (HDP 30.1895) and deprotected to result in HDP 30.2105.

HDP 30.2105

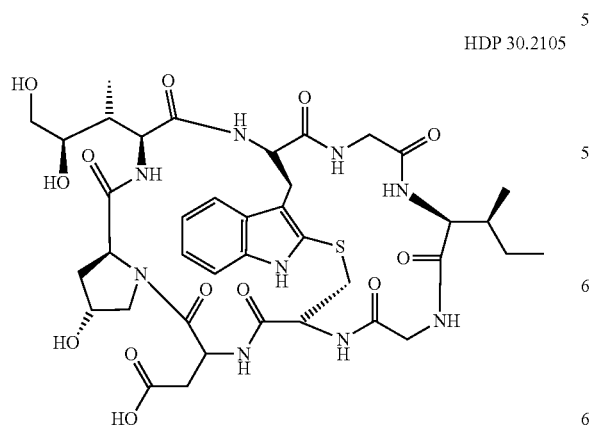

Step 1: 4-Hydroxy-pyrrolidine-1,2-dicarboxylic acid 2-allyl ester 1-(9H-fluoren-9-ylmethyl) ester (HDP 30.0013)

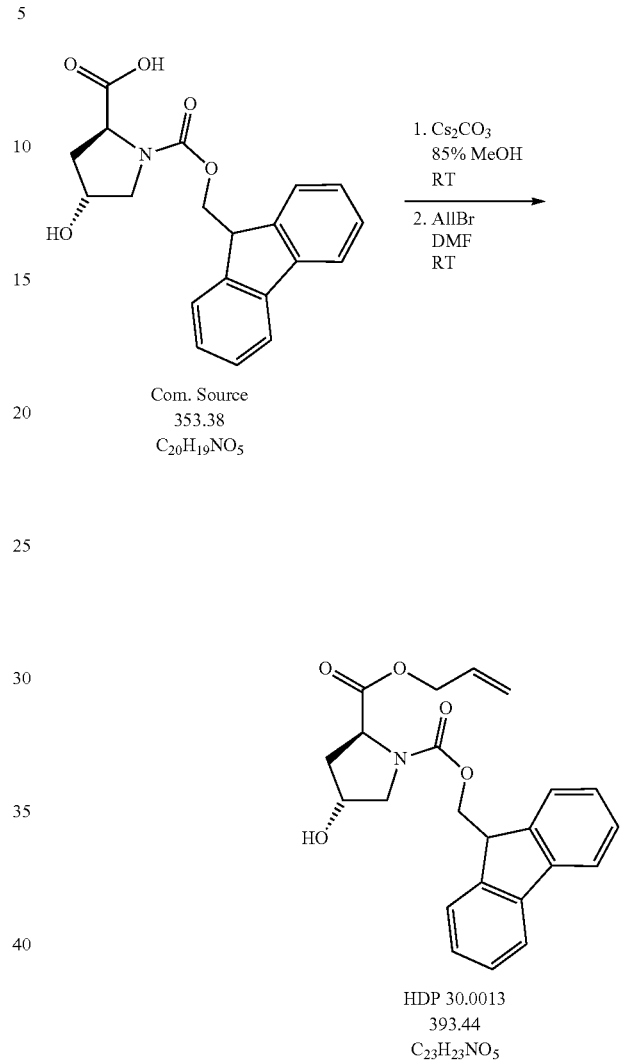

FmocHypOH (10.0 g, 28.3 mmol) was suspended in 100 ml 80% MeOH and Cs2CO3 (4.6 g, 14.1 mmol) was added. The suspension was stirred at 50° C. for 30 minutes until complete dissolution. The reaction mixture was concentrated to dryness and resolved in 100 ml DMF. Allylbromide (1.6 ml, 3.6 g, 29.7 mmol) was added dropwise and the reaction was stirred over night at RT. DMF was distilled off and the residue dissolved in tert-butylmethyl ether. Precipitates were filtered and the clear solution was absorbed on Celite prior column chromatography. The compound was purified on 220 g Silicagel with an n-hexane/ethyl acetate gradient.

Yield: 11.5 g, 100%

Step 2: Resin Loading (HDP 30.0400)

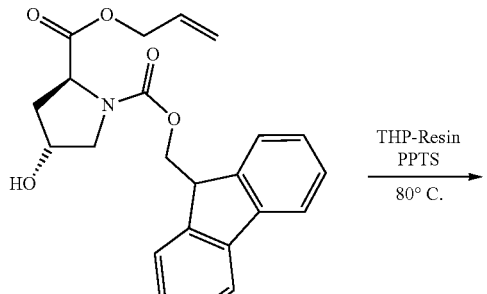

HDP 30.0013
393.44
C₂₃H₂₃NO₅

→ THP-Resin
PPTS
80° C.

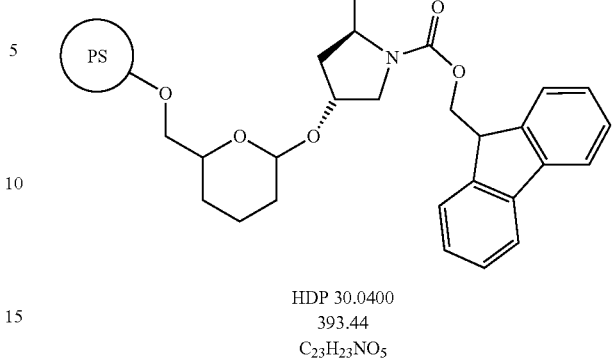

HDP 30.0400
393.44
C₂₃H₂₃NO₅

HDP 30.0013 (5.0 g, 14.1 mmol), pyridinium 4-toluenesulfonate (1.33 g, 5.3 mmol) were added to a suspension of 1,3-dihydro-2H-pyran-2-yl-methoxymethyl resin (5.0 g, 1.0 mmol/g THP-resin) in 40 ml dichloroethane. The reaction was stirred at 80° C. overnight. After cooling the resin was filtered and extensively washed with dichloroethane, dimethylformamide, acetonitrile, dichloromethane and tert-butylmethylether Loading was 0.62 mmol/g (determined by UV-spectroscopy of the fluorene methyl group after deprotection)

Step 3: Solid Phase Precursor Synthesis (HDP 30.1894)

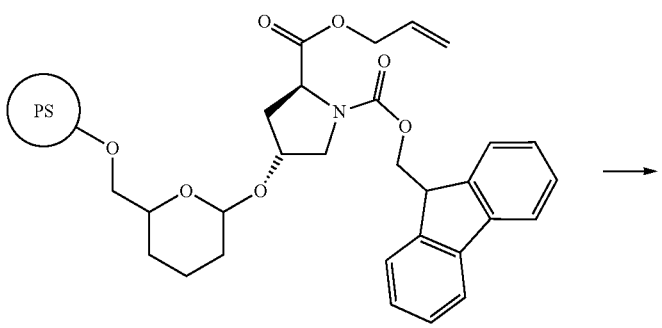

HDP 30.0400
393.44
C23H23NO5

→

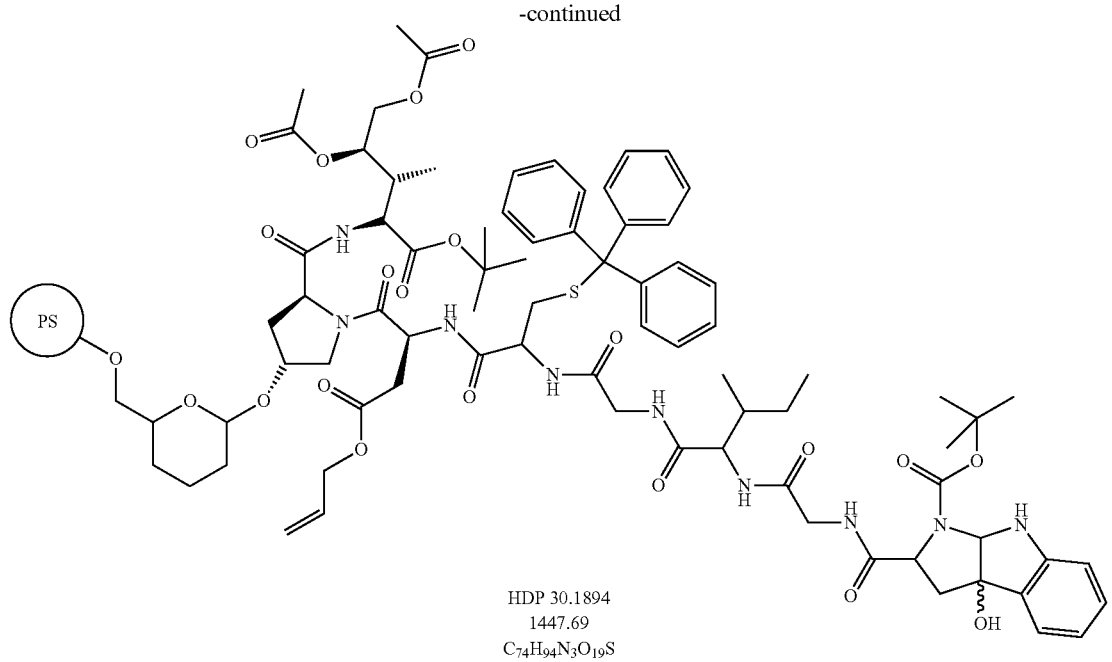

HDP 30.1894
1447.69
C$_{74}$H$_{94}$N$_3$O$_{19}$S

Resin Pre-Treatment:

HDP 30.0400 (0.5 g, 0.31 mmol) was treated with N,N-dimethylbarbituric acid (483 mg, 3.1 mmol) and Pd(PPh3)4 (69 mg, 0.06 mmol). The resin was shaken over night at RT. Thereafter the resin was extensively washed with dichloromethane, N-methyl-2-pyrrolidone, acetonitrile, dichloromethane and tert-butylmethyl ether and dried under reduced pressure.

Coupling Procedure:

All reactants and reagents were dissolved in dichloromethane/N-methyl-2-pyrrolidone containing 1% Triton-X100 (Solvent A).

HDP 30.0477 (257 mg, 0.38 mmol) was dissolved in 3.0 ml Solvent A and treated with 3.0 ml of a 0.2 N solution PyBOP (333 mg, 0.63 mmol, 2.0 eq), 3.0 ml of a 0.2 N solution HOBt (130 mg, 0.63 mmol, 2.0 eq) and 439 µl DIEA (4.0 eq). The reaction was heated to 50° C. for 8 minutes by microwave irradiation (20 W, CEM microwave reactor) and was washed with N-methyl-2-pyrrolidone after coupling.

Deprotection:

Deprotection was performed by addition of 6.0 ml 20% piperidine in N-methyl-2-pyrrolidone at 50° C. for 8 minutes. The resin was washed with N-methyl-2-pyrrolidone. (Note: No deprotection after coupling of the final amino acid)

All other amino acids were coupled following the above protocol, weightings are shown below:

0.63 mmol, 498 mg Fmoc Asp(OAll)OH 0.63 mmol, 738 mg Fmoc Cys(Tri)OH 0.63 mmol, 375 mg Fmoc GlyOH 0.63 mmol, 445 mg Fmoc IleOH 0.63 mmol, 375 mg Fmoc GlyOH 0.38 mmol, 242 mg N-Boc-HPIOH (HDP 30.0079)

4,5-Diacetoxy-2-amino-3-methyl-pentanoic acid tert-butyl ester; hydrochloride (HDP 30.0477) was synthesized as described in WO 2014/009025.

N-Boc-HPIOH (HDP 30.0079) was prepared according to Zanotti, Giancarlo; Birr Christian; Wieland Theodor; International Journal of Peptide & Protein Research 18 (1981) 162-8.

Step 4: HDP 30.1895

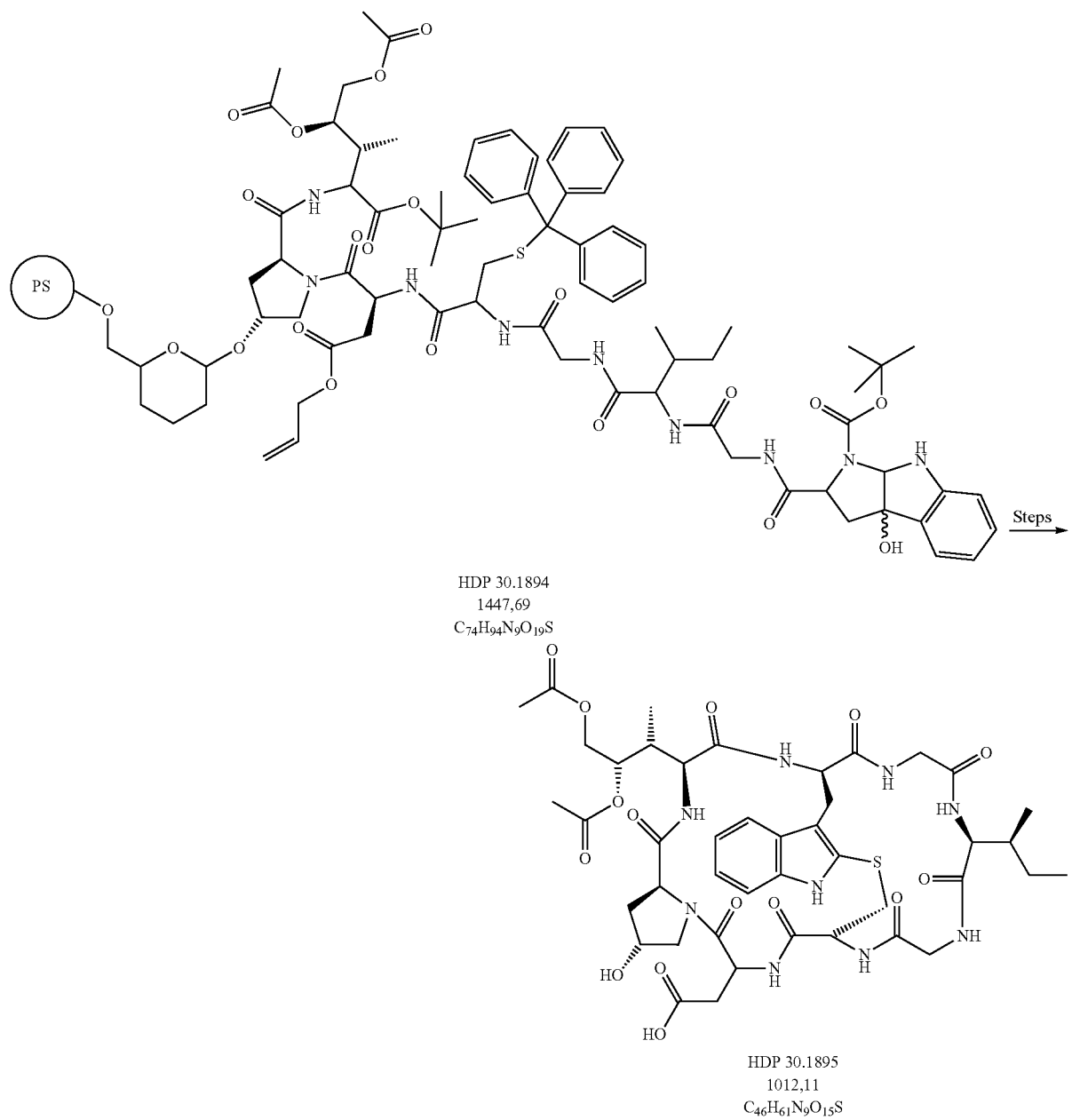

HDP 30.1894
1447,69
C<sub>74</sub>H<sub>94</sub>N<sub>9</sub>O<sub>19</sub>S

HDP 30.1895
1012,11
C<sub>46</sub>H<sub>61</sub>N<sub>9</sub>O<sub>15</sub>S

Elimination from Resin and B-Ring Formation

The resin was shaken with 10 ml trifluoroacetic acid containing 5% triisopropylsilane for 30 min and finally eluted into a 50 ml flask. The resin was washed twice with methanol (10 ml each). The combined eluates were concentrated in vacuum and re-suspended in 2-4 ml methanol. The methanolic solution was dropped twice into 50 ml cold diethyl ether for peptide precipitation. After centrifugation the precipitate was washed with diethyl ether (2 times) and dried under reduced pressure. The white precipitate was solubilized in approx. 4-5 mi methanol (0.5 ml per 100 mg) and purified by preparative reverse phase column chromatography. Approximately 100 mg crude precipitate were purified per run. Fractions were analyzed by mass spectrometry, combined and methanol distilled off under reduced pressure. The aqueous phase was freeze dried.

Yield: 24.4 mg, 23.7 μmol
Mass spectrometry: [M+H]$^+$, 1030.5

A-Ring Formation

The above freeze dried intermediate was dissolved in 25 ml dimethylformamide and treated with diphenylphosphorylazide (63 μl, 1185 μmol, 5 eq) and diisopropylethyl amine (201 μl, 1185 μmol, 5 eq). The reaction was stirred overnight (20 hours). Conversion was monitored by reverse phase chromatography and finally quenched with 100 μl water. The mixture was concentrated by reduced pressure and re-dissolved in 1-2 ml methanol. Precipitation of the product was performed by dropwise addition to 20 mi diethyl ether.

The precipitate was washed twice with diethyl ether and dried under reduced pressure. The next step was performed without further purification.

Mass spectrometry: [M+Na]$^+$, 1034.6

Ester Deprotection:

To the crude cyclisation product 2.5 ml dichloromethane, diethylbarbituric acid (22.3 mg, 118.5 µmol) and Pd(PPh$_3$)$_4$ (27 mg, 23.7 µmol) were added. The reaction was stirred at RT overnight. The reaction can be monitored by RP-HPLC. After complete conversion, the mixture was added dropwise to 20 ml cooled diethyl ether and the precipitate washed twice with diethyl ether. After drying at reduced pressure the precipitate was dissolved in methanol (1.0 ml) and purified by preparative reversed phase chromatography.

Yield: 15.0 mg

Mass spectrometry: [M+H]$^+$, 972.3; [M+Na]$^+$, 994.5

Step 5: HDP 30.2105

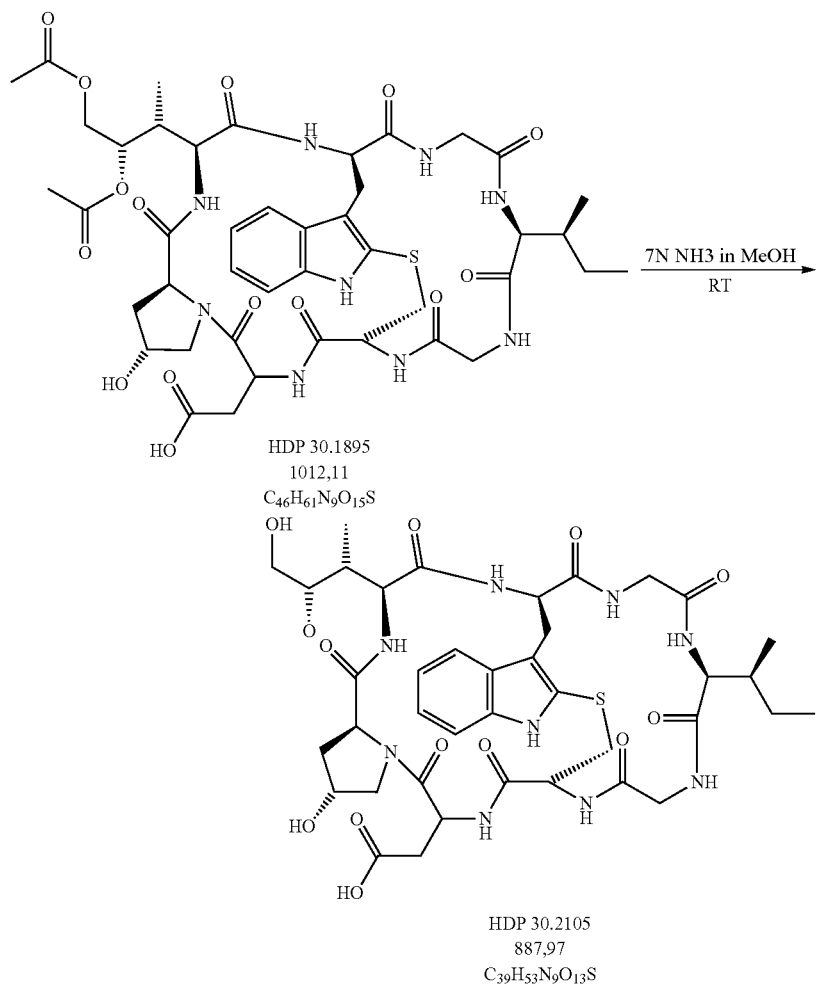

HDP 30.1895
1012,11
C$_{46}$H$_{61}$N$_9$O$_{15}$S

HDP 30.2105
887,97
C$_{39}$H$_{53}$N$_9$O$_{13}$S

HDP 30.1895 (15.0 mg, 15.3 µmol) was dissolved in 7 N methanolic NH$_3$ solution (3.0 ml) and stirred overnight. Conversion was checked by mass spectrometry. After complete conversion the reaction was concentrated in vacuum, suspended in 80% tert-butanol and lyophilized. Product was purified by preparative HPLC.

Yield: 12.1 mg

Mass spectrometry: [M+H]$^+$, 888.0; [M+Na]$^+$, 910.2

3. Synthesis of Synthetic Dideoxy Precursor HDP 30.2115

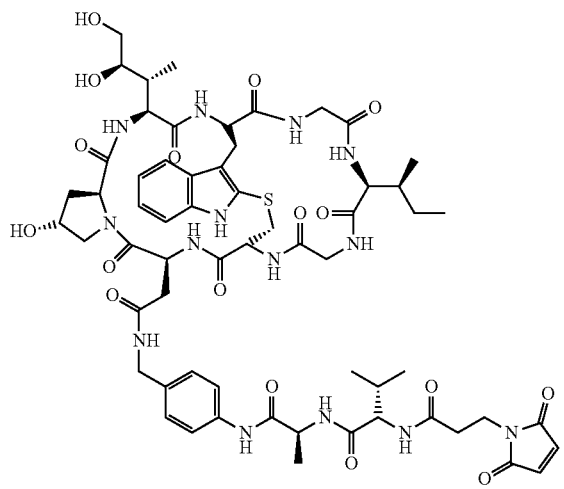

A dideoxy precursor molecule comprising a thiol reactive group with cleavable linker can be synthesized from example 2 product in 7 steps as follows:

Step 1: Fmoc-Val-OSu (HDP 30.1343)

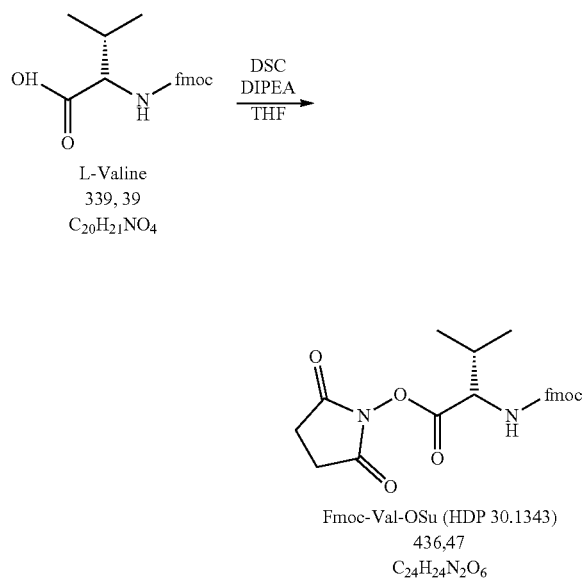

This compound is prepared according to R. A. Firestone et al, U.S. Pat. No. 6,214,345. Fmoc-Val-OH (20.24 g; 59.64 mmol) and N-hydroxysuccinimide (6.86 g=1.0 eq.) in tetrahydrofuran (200 ml) at 0° C. were treated with N,N'-dicyclohexylcarbodiimide (12.30 g; 1.0 eq.). The mixture was stirred at RT under argon atmosphere for 6 h and then the solid dicyclohexyl urea (DCU) by-product was filtered off and washed with THF and the solvent was removed by rotavap. The residue was dissolved in 300 ml dichloromethane, cooled in an ice bath for 1 h and filtered again to remove additional DCU. The dichloromethane was evaporated and the solid foam (26.51 g) was used in the next step without further purification.

Step 2: Fmoc-Val-Ala-OH (HDP 30.1414)

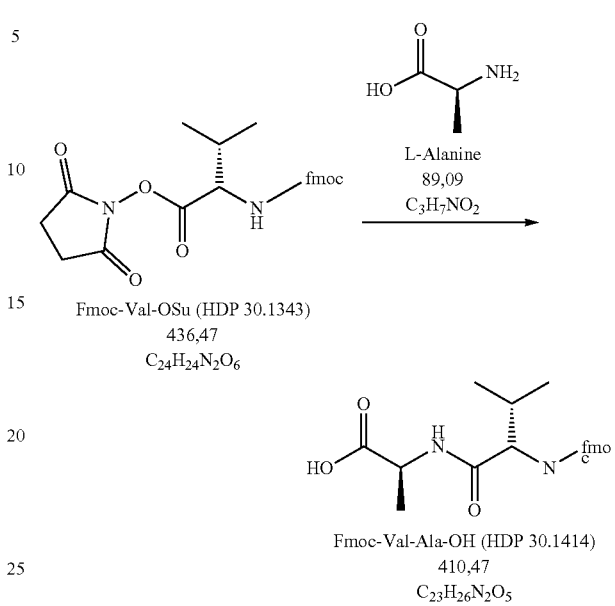

Step 2 product is prepared in analogy to P. W. Howard et al. US 2011/0256157. A solution of L-alanine (5.58 g; 1.05 eq.) and sodium hydrogen carbonate (5.51 g; 1.1 eq.) in 150 ml water was prepared and added to a solution of HDP 30.1343 (26.51 g; max. 59.6 mmol) in 225 ml tetrahydrofuran. The mixture was stirred for 50 h at RT. After consumption of starting material the solution was partitioned between 240 ml of 0.2 M citric acid and 200 ml of ethyl acetate. The aqueous layer was separated and extracted with ethyl acetate (3×200 ml). The combined organic layers were washed with water and brine (300 ml each) dried (MgSO$_4$) and the solvent was evaporated to approx. 200 ml. Pure product precipitated at this time and was filtered off. The mother liquor was evaporated to dryness and the residue was stirred 1 h with 100 ml MTBE to result additional crystalline material. The two crops of product were combined to 18.01 g (74%) white powder. (m.p.: 203-207° C.)

MS (ESI+) [M+Na]$^+$ found: 410.94; calc.: 411.19 (C$_{23}$H$_{27}$N$_2$O$_5$).
[M+Na]$^+$ found: 433.14; calc.: 433.17 (C$_{23}$H$_{27}$N$_2$O$_5$).
[2M+H]$^+$ found: 842.70; calc.: 843.36 (C$_{46}$H$_{52}$N$_4$NaO$_{10}$).

Step 3: Fmoc-Val-Ala-PAB-NHBoc (HDP 30.1713)

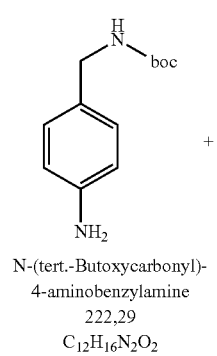

N-(tert.-Butoxycarbonyl)-
4-aminobenzylamine
222,29
C$_{12}$H$_{16}$N$_2$O$_2$

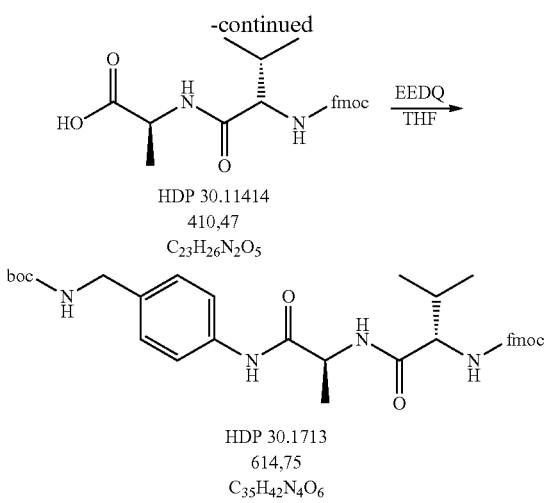

HDP 30.11414
410,47
C₂₃H₂₆N₂O₅

HDP 30.1713
614,75
C₃₅H₄₂N₄O₆

Step 2 product HDP 30.1414 (1.76 g; 4.28 mmol) and 4-[(N-Boc)aminomethyl]aniline (1.00 g; 1.05 eq.) were dissolved in 26 ml abs. tetrahydrofuran. 2-Ethoxy-N-(ethoxycarbonyl)-1,2-dihydroquinoline (EEDQ 1.11 g; 1.05 eq.) was added and the mixture was stirred at RT, protected from light. With ongoing reaction a gelatinous matter is formed from the initially clear solution. After 40 h the reaction mixture was diluted with 25 ml of tert-butylmethyl ether (MTBE) and stirred for 1 h. Subsequently the precipitation is filtered off with suction, washed with MTBE and dried in vacuo to 2.30 g (85% yield) of a white solid.

¹H NMR (500 MHz, DMSO-d6) δ 9.87 (s, 1H), 8.11 (d, J=7.1 Hz, 1H), 7.88 (d, J=7.5 Hz, 2H), 7.74 (q, J=8.4, 7.9 Hz, 2H), 7.51 (d, J=8.2 Hz, 2H), 7.45-7.23 (m, 7H), 7.17 (d, J=8.3 Hz, 2H), 4.44 (p, J=7.0 Hz, 1H), 4.36-4.17 (m, 3H), 3.96-3.89 (m, 1H), 2.01 (hept, J=6.9 Hz, 1H), 1.39 (s, 9H), 1.31 (d, J=7.1 Hz, 3H), 0.90 (d, J=6.8 Hz, 3H), 0.87 (d, J=6.8 Hz, 3H).

¹³C NMR (126 MHz, DMSO-d6) δ 170.84, 170.76, 156.04, 155.63, 143.77, 143.69, 140.60, 137.41, 134.99, 127.50, 127.26, 126.93, 125.22, 119.95, 118.97, 77.60, 65.62, 59.95, 48.86, 46.62, 42.93, 30.28, 28.16, 19.06, 18.10, 18.03.

Step 4: H-Val-Ala-PAB-NHBoc (HDP 30.1747)

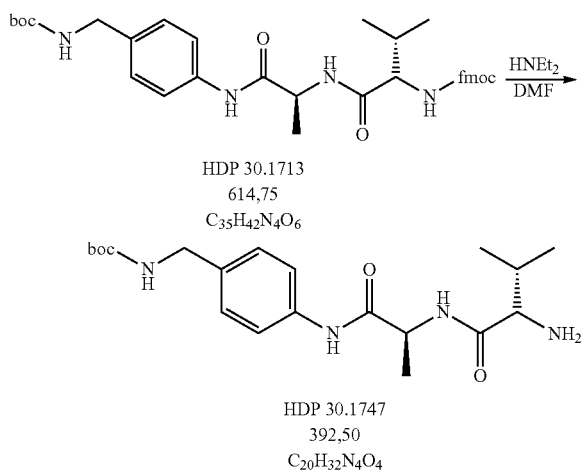

HDP 30.1713
614,75
C₃₅H₄₂N₄O₆

HDP 30.1747
392,50
C₂₀H₃₂N₄O₄

Step 3 compound HDP 30.1713 (1.230 g, 2.00 mmol) was placed in a 100 ml flask and dissolved in 40 ml dimethylformamide (DMF). Diethyl amine (7.5 ml) was added and the mixture was stirred at RT. The reaction was monitored by TLC (chloroform/methanol/HOAc 90:8:2). After consumption of starting material (30 min) the volatiles were evaporated and the residue was co-evaporated with 40 ml fresh DMF to remove traces of diethyl amine. The crude product was used without further purification for the next step.

MS (ESI+) [MH]⁺ found: 393.26; calc.: 393.25 (C₂₀H₃₃N₄O₄).
[M+Na]⁺ found: 415.35; calc.: 415.23 (C₂₀H₃₂N₄NaO₄).
[2M+H]⁺ found: 785.37; calc.: 785.49 (C₄₀H₆₆N₈O₈).

Step 5: BMP-Val-Ala-PAB-NHBoc (HDP 30.2108)

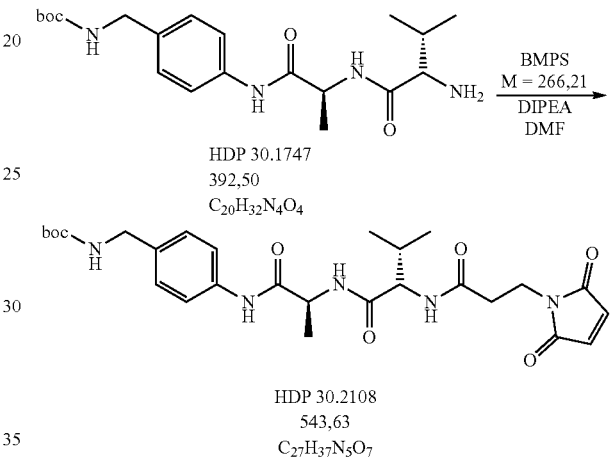

HDP 30.1747
392,50
C₂₀H₃₂N₄O₄

HDP 30.2108
543,63
C₂₇H₃₇N₅O₇

Crude step 4 product HDP 30.1747 (max 2.00 mmol) was dissolved in 40 ml DMF, 3-(maleimido)propionic acid N-hydroxysuccinimide ester (BMPS 532 mg; 1.0 eq.) and N-ethyldiisopropylamine (510 µl, 1.5 eq.) were added and the mixture was stirred 3 h at RT After consumption of starting material HDP 30.1747 (TLC: chloroform/methanol/HOAc 90:8:2) the volatiles were evaporated and the residue is stirred with 50 ml MTBE until a fine suspension was formed (1 h). The precipitate was filtered off with suction, washed with MTBE and dried. The crude product (1.10 g) was dissolved in 20 ml dichloromethane/methanol 1:1, kieselgur (15 g) was added and the solvents were stripped off. The solid material was placed on top of an 80 g silica gel column and eluted with a linear gradient of 0-10% methanol in dichloromethane. Product fractions were combined and evaporated to 793 mg (73% over two steps) amorphous solid.

MS (ESI⁺) [M+Na]⁺ found: 566.24; calc.: 566.26 (C₂₇H₃₇N₆NaO₇).

¹H NMR (500 MHz, DMSO-d6) δ 9.75 (s, 1H), 8.09 (d, J=7.1 Hz, 1H), 7.98 (d, J=8.4 Hz, 1H), 7.52 (d, J=8.6 Hz, 2H), 7.29-7.23 (m, 1H), 7.16 (d, J=8.5 Hz, 2H), 6.98 (s, 2H), 4.39 (p, J=7.1 Hz, 1H), 4.13 (dd, J=8.4, 6.7 Hz, 1H), 4.06 (d, J=6.1 Hz, 2H), 3.67-3.56 (m, 2H), 2.49-2.41 (m, 2H), 1.96 (h, J=6.8 Hz, 1H), 1.39 (s, 9H), 1.30 (d, J=7.1 Hz, 3H), 0.86 (d, J=6.8 Hz, 3H), 0.82 (d, J=6.8 Hz, 3H).

¹³C NMR (126 MHz, DMSO-d6) δ 170.80, 170.63, 170.60, 169.72, 155.65, 137.45, 134.94, 134.44, 127.26, 118.95, 77.62, 57.71, 48.92, 42.95, 33.96, 33.64, 30.17, 28.17, 19.02, 18.06, 17.82.

Step 6: BMP-Val-Ala-PAB-NH$_2$ (HDP 30.2109)

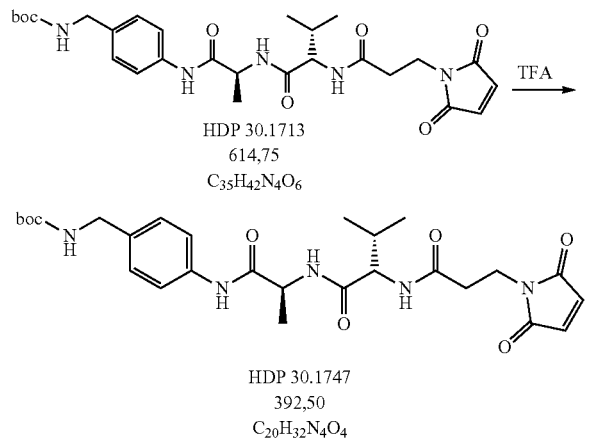

Step 5 product HDP 30.2108 (400 mg, 736 μmol) was dissolved in 4.000 μl trifluoroacetic acid and stirred for 2 min. Subsequently the volatiles were evaporated at RT and the remainders were co-evaporated twice with 4,000 μl toluene. The residue was dissolved in 5,000 μl 1,4-dioxane/water 4:1, solidified in liquid nitrogen and freeze-dried: 410 mg (quant.) colorless powder MS (ESI$^+$) [M+Na]$^+$ found: 415.35; calc.: 466.21 (C$_{22}$H$_{29}$N$_6$NaO$_6$).

[2M+H]$^+$ found: 887.13; calc.: 887.44 (C$_{44}$H$_{59}$N$_{10}$O$_{10}$).

$^1$H NMR (500 MHz, DMSO-d6) δ 9.89 (s, 1H), 8.13 (d, J=6.9 Hz, 1H), 7.99 (d, J=8.2 Hz, 1H), 7.66-7.60 (m, 2H), 7.41-7.34 (m, 2H), 6.98 (s, 2H), 4.39 (p, J=7.1 Hz, 1H), 4.11 (dd, J=8.2, 6.6 Hz, 1H), 3.97 (q, J=5.6 Hz, 2H), 3.69-3.58 (m, 2H), 2.49-2.40 (m, 2H), 1.96 (h, J=6.8 Hz, 1H), 1.32 (d, J=7.1 Hz, 3H), 0.86 (d, J=6.8 Hz, 3H), 0.83 (d, J=6.7 Hz, 3H).

$^{13}$C NMR (126 MHz, DMSO-d6) δ 171.24, 170.78, 170.72, 169.85, 158.12 (q, J=33.2 Hz, TFA), 158.25, 157.99, 157.73, 139.19, 134.53, 129.45, 128.52, 119.02, 116.57 (q, J=296.7 Hz, TFA), 57.78, 49.08, 41.90, 34.00, 33.68, 30.21, 19.07, 18.16, 17.76.

Step 6: HDP 30.2115

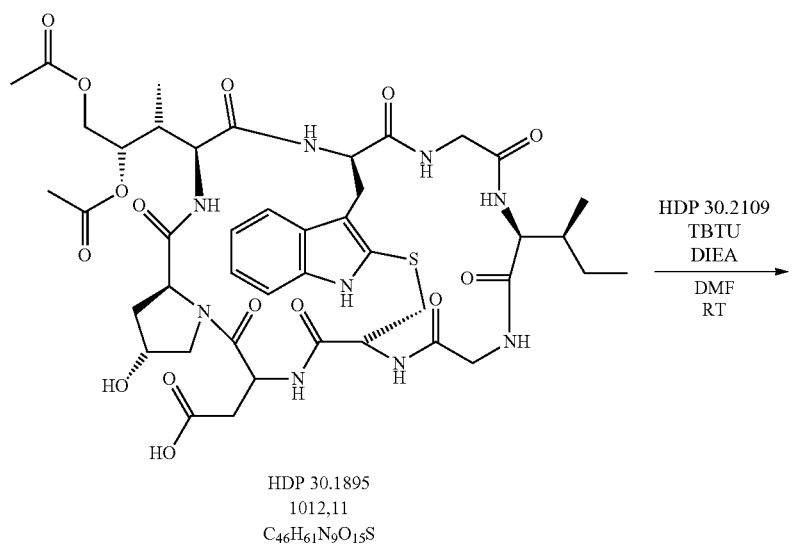

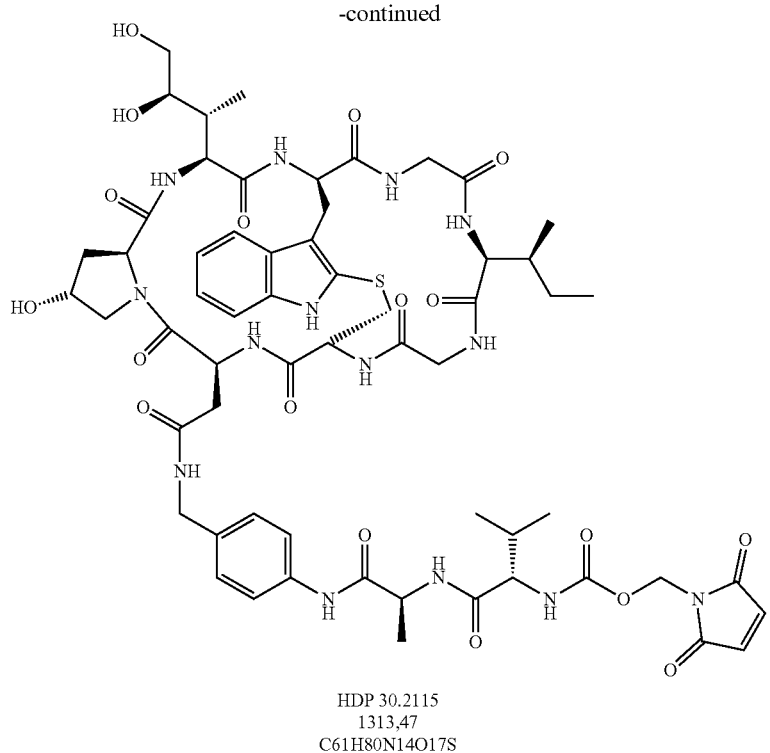

HDP 30.2115
1313,47
C61H80N14O17S

HDP 30.2105 (15.0 mg, 16.5 µmol) were treated with 429 µl of a 0.1 M solution of HDP 30.2109 (25.2 µmol, 1.5 eq), 492 µl of 0.1 M TBTU (25.2 µmol, 1.5 eq) and 492 µl of 0.2 M DIEA (49.1 µmol, 3.0 eq) at RT. The reaction was monitored by RP-HPLC. After completion the reaction was quenched with 100 µl H$_2$O stirred for 15 minutes and injected onto a preparative RP-HPLC.

Yield: 12.2 mg, 56%

Mass spectrometry: 1313.2 [M+H]$^+$, 1335.5 [M+Na]$^+$

4. Synthesis of Synthetic Dideoxy Precursor HDP 2179

4.1 Synthesis of HDP 30.2179

HDP 30.2179

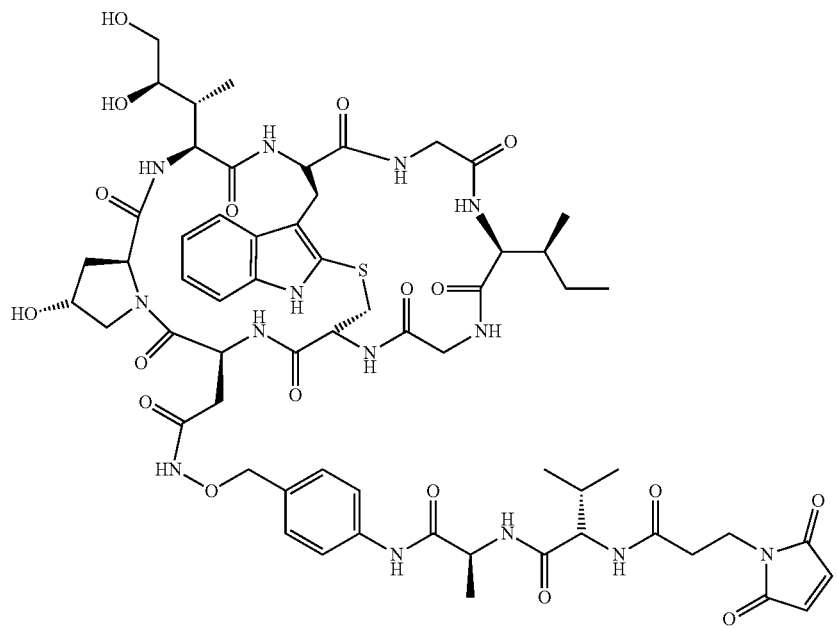

4.2 Synthesis of HDP 30.2007

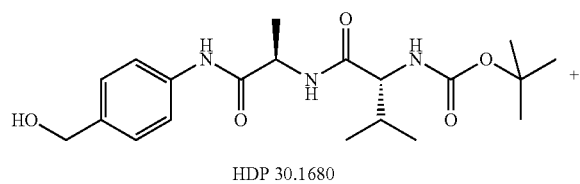

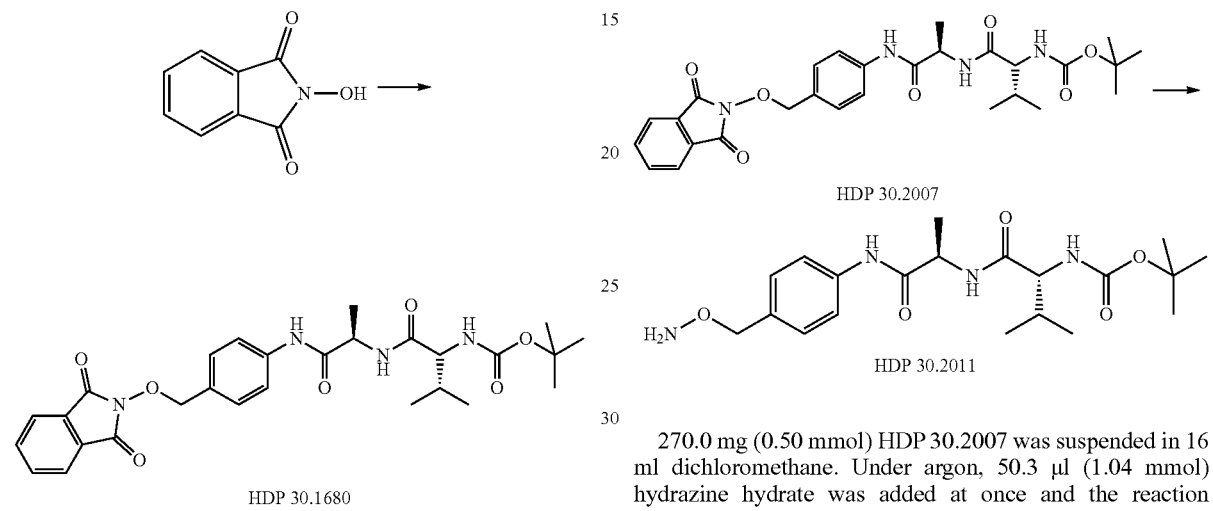

770.0 mg (1.96 mmol) HDP 30.1960, prepared according to EP 15 000 681.5, 319.2 mg (1.96 mmol) N-hydroxyphthalimide and 513.3 (1.96 mmol) triphenylphosphine were dissolved in 40 ml dry tetrahydrofuran. Under argon 889.2 µl (1.96 mmol) of an ethyl diazocarboxylate solution in toluene (40%) were added over 30 min. The reaction mixture was stirred for 24 h at RT and evaporated to dryness. The solid residue was purified on a silica-gel-column with a gradient from CHCl$_3$ to CHCl$_3$/MeOH (30/1) as eluent. Crude HDP 30.2007 was obtained as a yellow solid. The crude product was further purified on a silica-gel-column with a gradient from n-hexane to n-hexane/ethyl acetate/methanol (10/10/1) as eluent. HDP 30.2007 was obtained as a white solid. Yield: 270.0 mg (22%).

MS (ESI$^+$) found: 561.14 [M+Na]$^+$: calc.: 561.24 (C$_{28}$H$_{34}$N$_4$NaO$_7$).

MS (ESI$^+$) found: 1099.70 2 [M+Na]$^+$; calc.: 1099.48 (C$_{56}$H$_{68}$N$_8$NaO$_{14}$).

4.3 Synthesis of HDP 30.2011

270.0 mg (0.50 mmol) HDP 30.2007 was suspended in 16 ml dichloromethane. Under argon, 50.3 µl (1.04 mmol) hydrazine hydrate was added at once and the reaction mixture stirred for 24 h under argon and RT. The suspension was filtered and the solid washed with dichloromethane. The filtrates were evaporated and the residue dried in high vacuum. HDP 30.2011 was obtained as a white solid and was used for the next steps without further purification. Yield: 199.0 mg (97%).

MS (ESI$^+$) found: 431.50 [M+Na]$^+$, calc.: 431.24 (C$_{20}$H$_{32}$N$_4$NaO$_5$).

4.4 Synthesis of HDP 30.2177

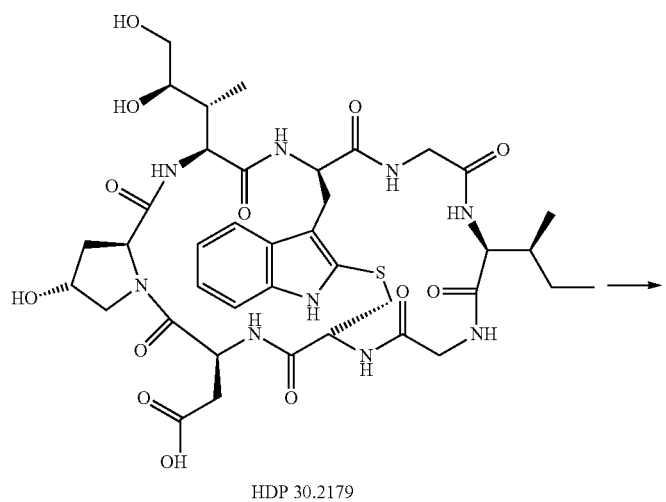

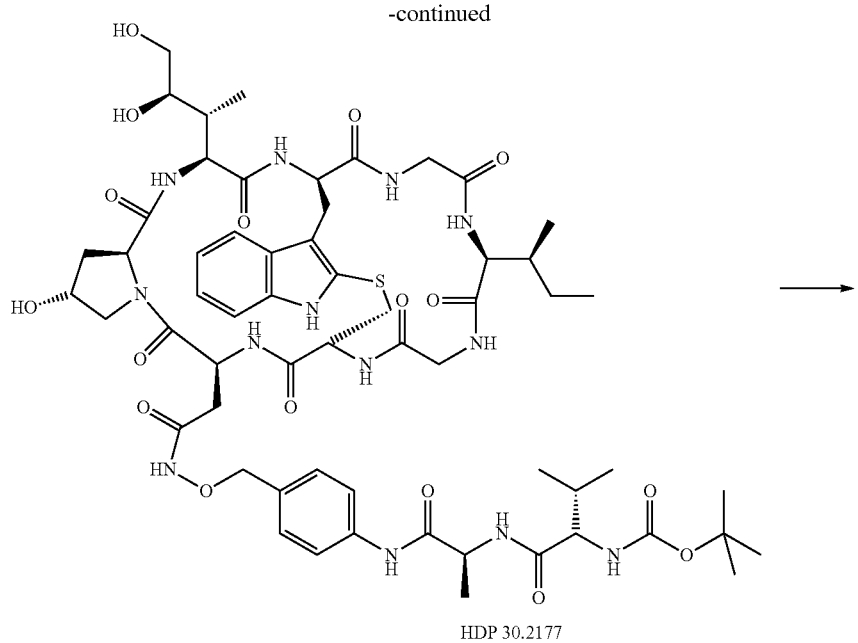

HDP 30.2177

20.59 mg (23.17 μmol) HDP 30.2105 was dissolved in 1,200 ml dry dimethylformamide (DMF). The solution was purged with argon and treated with 18.85 mg (46.10 μmol) HDP 30.2011 dissolved in dry dimethylformamide (DMF), 24.05 mg (46.10 μmol) PyBOP (benzotriazol-1-yl-oxytripyrrolidinophosphonium hexafluorophosphate) dissolved in 450 ml dry dimethylformamide (DMF) and 86.20 μl (82.30 mmol) N-ethyl-diisopropylamine (DIPEA) solution in DMF (100 μl DIPEA dissolved in 500 μl DMF). The reaction mixture was stirred at RT under argon. After 5 h the reaction volume was diluted with cold methyl-t-butylether (MTBE). The white precipitate was centrifuged and washed with cold MTBE. The crude solid was purified by RP18 HPLC (Luna™ 10 μ, 250×21 mm, Phenomenex®, 290 nm) with a gradient of 95% $H_2O$/5% MeOH to 95% MeOH/5% $H_2O$ and a flow rate of 15 ml/min. The product fraction at 17.5 min was collected, evaporated and freeze dried in water to 13.84 mg (47%) HDP 30.2177 as a white, amorphous solid.

MS (ESI$^+$) found: 1278.45 [MH]$^+$; calc.: 1277.58 ($C_{59}H_{63}N_{13}O_{17}S$).

MS (ESI$^+$) found: 1300.84 [M+Na]$^+$; calc.: 1300.58 ($C_{59}H_{83}N_{13}NaO_{17}S$).

4.5 Synthesis of HDP 30.2179

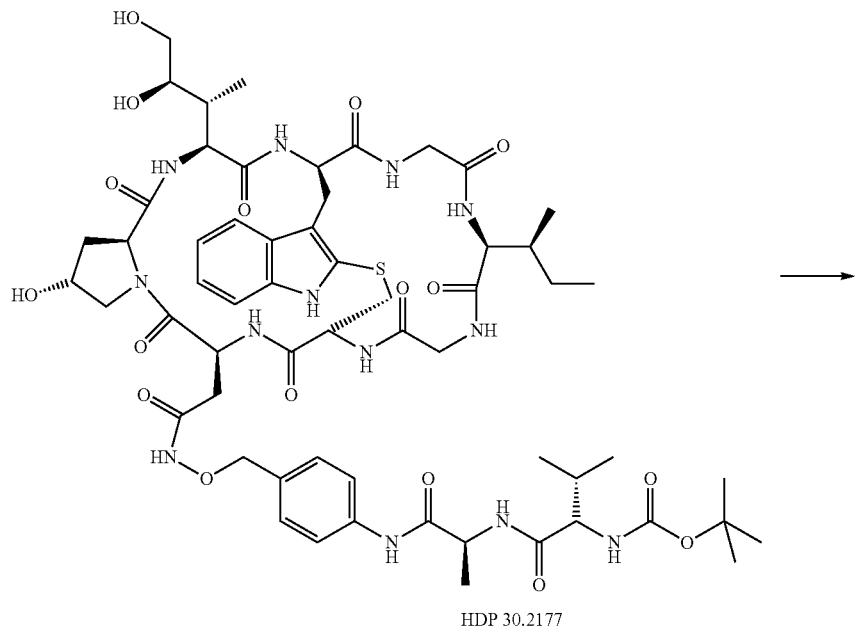

HDP 30.2177

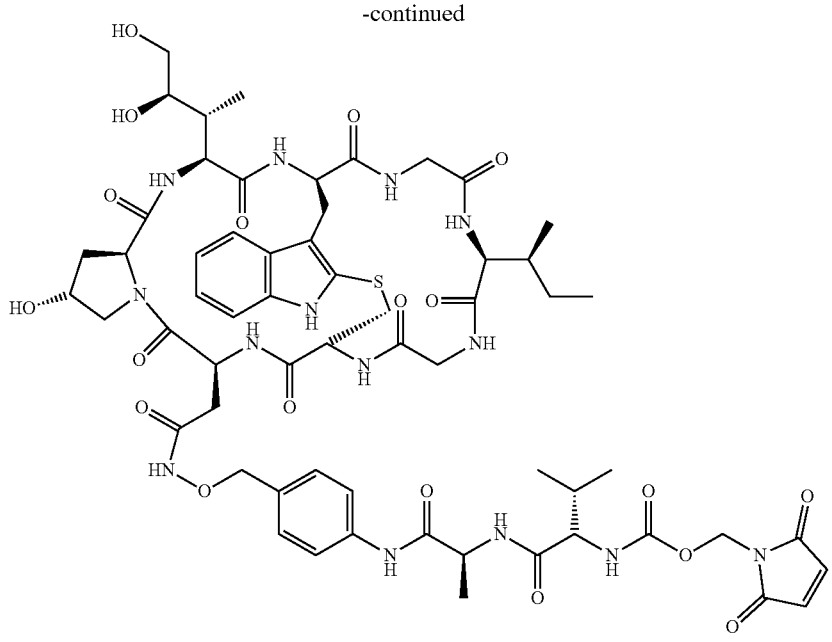

HDP 30.2179

13.84 mg (10.82 µmol) HDP 30.2177 was dissolved in 2,000 µl trifluoroacetic acid (TFA) and stirred for 5 minutes at RT. Excess TFA was removed with a rotary evaporator at 33° C. water bath temperature and the remaining residue treated with 5 ml of methanol and evaporated to dryness. The oily residue was dried in high vacuum, forming a white solid. The solid was dissolved in 1,700 µl dry dimethylformamide (DMF) and treated with 5.77 mg (21.67 µmol) N-Succinimidyl Maleimidopropionate (BMPS). 75.40 µl DIPEA solution (50 µl DIPEA dissolved in 450 µl dry DMF) was added. The reaction mixture was stirred under argon for 5 h and treated with 20 ml of cold MTBE. The precipitate was centrifuged, washed with cold MTBE and dried. The crude product was purified by RP18 HPLC (Luna™ 10µ, 250×21 mm, Phenomenex®, 290 nm) with a gradient of 95% $H_2O$/5% MeOH to 95% MeOH/5% $H_2O$ and a flow rate of 15 ml/min. The product fraction at 14.5 minutes was collected, evaporated and freeze dried in water to yield 7.40 mg (51%) HDP 30.2179 as a white, amorphous solid.

MS (ESI$^+$) found: 1351.50 [M+Na]$^+$; calc.: 1351.55 ($C_{61}H_{80}N_{14}NaO_{18}S$).

Furthermore, an alternative dideoxy precursor molecule comprising a —CO—NHOH group instead of the carboxamide group at amino acid 1 can be synthesized for example by reacting the carboxylate precursor HDP 30.2105 with O-benzyl hydroxylamine under standard condensation conditions (PyBOP, DCC, mixed anhydride etc.). The benzylic group of the so obtained O-benzyl hydroxamic acid derivative of HDP 30.2105 can easily be removed under catalytic hydrogenolytic conditions (Pd/H2), forming the free —CO—NHOH group. This acidic hydroxamic function can then be alkylated to —CO—NHOR with different halogenated or O-tosylated alkyl-linker building blocks. This alkylation takes place under basic conditions with LIOH, NaOH, KO-t-Bu or other suitable bases.

5. Synthesis of Synthetic Dideoxy Precursor HDP 30.2191

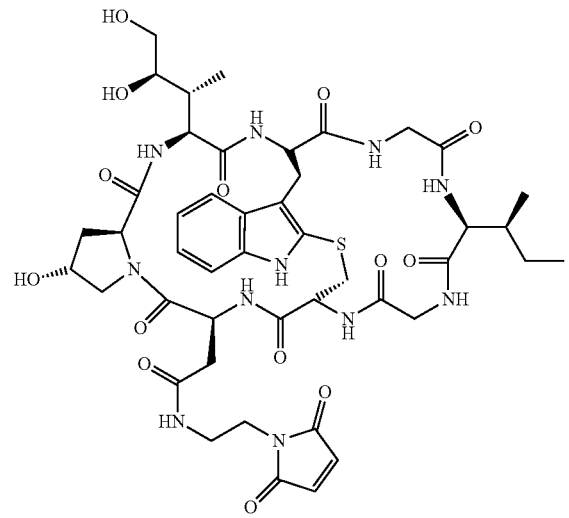

A dideoxy precursor molecule comprising a thiol reactive group with stable linker can be synthesized from example 2 product as follows:

Example 2 product (HDP 30.2105), 11.00 mg (12.39 µmol) was dissolved in 123.9 µl dry DMF. Subsequently 1 M solutions of N-hydroxysuccinimide and diisopropylcarbodiimide in DMF (123.9 µl, 10 eq. each) were added. After 1 h at RT a 1 M solution of N-(2-aminoethyl)maleimide trifluoroacetate salt in DMF was added and the reaction mixture was stirred for additional 4 h. Then the reaction mixture was dropped in 10 ml of MTBE at 0° C. The resulting precipitate was collected by centrifugation and washed with additional 10 ml of MTBE. The residue was purified by preparative HPLC on a C18 column with a gradient from 5-100% methanol. The product containing fractions evaporated and lyophilized from t-butanol/water to result 9.27 mg (54%) title compound as colorless powder MS (ESI$^+$) [MH]$^+$ found: 1010.3; calc.: 1010.4 ($C_{45}H_{60}N_{11}O_{14}S$).

[M+Na]+ found 1032.5; calc.: 1032.39 (C$_{45}$H$_{59}$N$_{11}$NaO$_{14}$S).

6. Synthesis of Synthetic Dideoxy Precursor HDP 30.2157

A dideoxy precursor molecule comprising a thiol reactive group with reducible linker can be synthesized from example 2 product as follows:

Step 1

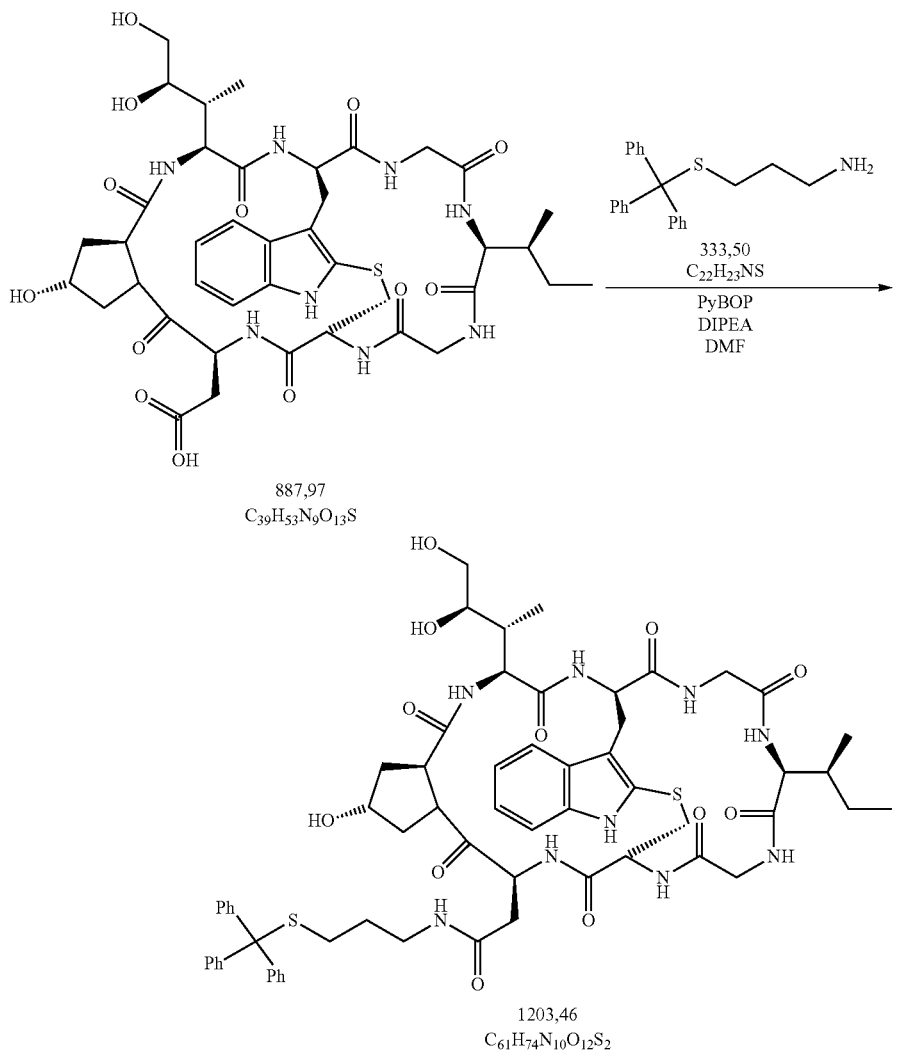

Example 2 product (HDP 30.2105), 11.36 mg (12.97 µmol) is dissolved in 512 µl dry DMF. Subsequently A 0.1M solutions of PyBOP in DMF (512 µl, 4 eq.) and 8.70 µl (4 eq.) DIPEA were added. After 1 min a 0.1M solution of 3-[(triphenylmethyl)sulfanyl]propan-1-amine in dichloromethane is added and the reaction mixture was stirred for additional 3.5 h. Then the reaction mixture was dropped in 10 ml of MTBE at 0° C. The resulted precipitate was collected by centrifugation and washed with additional 10 ml of MTBE. The residue was purified by preparative HPLC on a C18 column with a gradient from 5-100% methanol. The product containing fractions evaporated and lyophilized from t-butanol/water 4:1 to result 9.52 mg (62%) product as amorphous solid.

MS (ESI+) [M+Na]+ found: 1225.30; calc.: 1225.48 (C$_{61}$H$_{74}$N$_{10}$NaO$_{12}$S$_2$).

Step 2

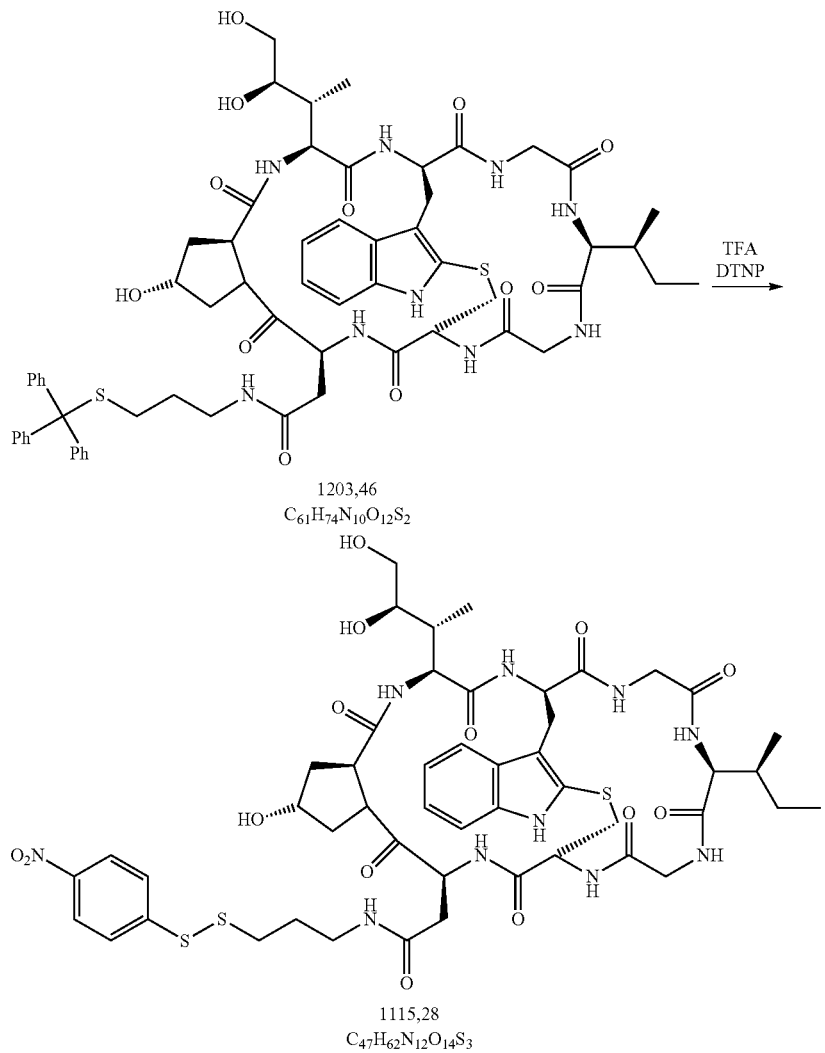

To step 1 product (9.52 mg, 7.91 μmol) a 0.5 M solution of 2,2'-dithiobis(5-nitropyridine), DTNP in trifluoroacetic acid (79.1 μl, 5 eq.) was added. After 4 min the reaction mixture was precipitated in 10 ml of MTBE at 0° C. The resulting solids were collected by centrifugation and washed with additional 10 ml of MTBE. The crude product was purified by preparative HPLC on a C18 column with a gradient from 5-100% methanol with 0.05 TFA. The pure fraction was evaporated and the residue lyophilized from 2 ml t-butanol/water 4:1 to give 7.48 mg (85%) HDP 30.2157 as a slightly yellowish powder.

MS (ESI$^-$) 1146.97 [M+H]$^+$, 1169.17 [M+Na]$^+$

7. Synthesis of Conjugate chiBCE19-D265C-30.2115

Conjugation of HDP 30.2115 to 10 mg chiBCE19-D265C
10 mg Thiomab chiBCE19-D265C in PBS buffer will be used for conjugation to HDP 30.2115.

Adjust antibody solution to 1 mM EDTA:
  2 ml antibody solution (10.0 mg)+20 μl 100 mM EDTA, pH 8.0
Amount antibody: 10 mg=6.8×10$^{-8}$ mol
Uncapping of cysteines by reaction of antibody with 40 eq. TCEP:
  2 ml antibody solution (6.8×10$^{-8}$ mol)+54.5 μl 50 mM TCEP solution (2.72×10$^{-6}$ mol)
  Incubate for 3 h at 37° C. on a shaker.
Two consecutive dialyses at 4° C. in 2.0l 1×PBS, 1 mM EDTA, pH 7.4 in a Slide-A-Lyzer Dialysis Cassette 20,000 MWCO, first dialysis ca. 4 h, second dialysis overnight
Concentrate to ca. 4.0 ml using Amicon Ultra Centrifugal Filters 50,000 MWCO.
Oxidation by reaction of antibody with 20 eq. dehydroascorbic acid (dhAA):
  ca. 2 ml antibody solution (6.8×10$^{-8}$ mol)+27.2 μl fresh 50 mM dhAA solution (1.36×10$^{-6}$ mol)
  Incubate for 3 h at RT on a shaker.
Conjugation with amanitin using 6 eq. HDP 30.2115 and quenching with 25 eq. N-acetyl-L-cysteine:
  Solubilize 0.7 mg HDP 30.2115 in 70 μl DMSO=10 μg/μl
  ca. 2 ml antibody solution (=9.5 mg; 6.46×10$^{-8}$ mol)+50.9 μl HDP 30.2115 (=509 μg; 3.88×10$^{-7}$ mol).
  Incubate 1 h at RT.
  Quench by addition of 16 μl 100 mM N-acetyl-L-cysteine (1.62×10$^{-6}$ mol).

Incubate 15 min at RT (or overnight at 4° C.).

Purify each reaction mix with PD-10 columns equilibrated with 1×PBS, pH 7.4. Identify protein-containing fractions with Bradford reagent on parafilm and bring protein-containing fractions together.

Dialysis of each antibody solution at 4° C. overnight in 2.0 l PBS, pH 7.4 and Slide-A-Lyzer Dialysis Cassettes 20'000 MWCO.

Determination of protein concentration and drug-antibody ratio (DAR) by UV-spectra (absorption at 280 nm and 310 nm) using naked antibody vs. ADC adjusted to identical protein concentrations.

Adjust protein concentration to 5.0 mg/ml ($3.4 \times 10^{-5}$ M) and bring to sterile conditions by filtration. Store at 4° C.

8. Synthesis of Conjugate chiBCE19-D265C-30.2179

Conjugation of HDP 30.2179 to 10 mg chiBCE19-D265C 10 mg of the Thiomab chiBCE19-D265C in PBS buffer will be used for conjugation to HDP 30.2179.

Adjust antibody solution to 1 mM EDTA:
2 ml antibody solution (10.0 mg)+20 µl 100 mM EDTA, pH 8.0

Amount antibody: 10 mg=$6.8 \times 10^{-8}$ mol

Uncapping of cysteines by reaction of antibody with 40 eq. TCEP:
2 ml antibody solution ($6.8 \times 10^{-8}$ mol)+54.5 µl 50 mM TCEP solution ($2.72 \times 10^{-6}$ mol)

Incubate for 3 h at 37° C. on a shaker.

Two consecutive dialyses at 4° C. in 2.0 l 1×PBS. 1 mM EDTA, pH 7.4 in a Slide-A-Lyzer Dialysis Cassette 20,000 MWCO, first dialysis ca. 4 h, second dialysis overnight Concentrate to ca. 4.0 ml using Amicon Ultra Centrifugal Filters 50'000 MWCO.

Oxidation by reaction of antibody with 20 eq. dehydroascorbic acid (dhAA):
ca. 2 ml antibody solution ($6.8 \times 10^{-8}$ mol)+27.2 µl fresh 50 mM dhAA solution ($1.36 \times 10^{-6}$ mol)

Incubate for 3 h at RT on a shaker.

Conjugation with amanitin using 6 eq. HOP 30.2179 and quenching with 25 eq. N-acetyl-L-cysteine:
Solubilize 0.7 mg of HOP 30.2179 in 70 µl DMSO=10 µg/µl
ca. 2 ml antibody solution (=9.5 mg; $6.46 \times 10^{-8}$ mol)+51.5 µl HDP 30.2179 (=515 µg; $3.88 \times 10^{-7}$ mol).

Incubate 1 h at RT.

Quench by addition of 16 µl 100 mM N-acetyl-L-cysteine ($1.62 \times 10^{-6}$ mop.

Incubate 15 min at RT (or overnight at 4° C.).

Purify each reaction mix with PD-10 columns equilibrated with 1×PBS, pH 7.4. Identify protein-containing fractions with Bradford reagent on parafilm and bring protein-containing fractions together.

Dialysis of each antibody solution at 4° C. overnight in 2.0 l PBS, pH 7.4 and Slide-A-Lyzer Dialysis Cassettes 20'000 MWCO.

Determination of protein concentration and drug-antibody ratio (DAR) by UV-spectra (absorption at 280 nm and 310 nm) using naked antibody vs. ADC adjusted to identical protein concentrations.

Adjust protein concentration to 5.0 mg/ml ($3.4 \times 10^{-5}$M) and bring to sterile conditions by filtration. Store at 4° C.

9. Conjugation of HOP 30.2115 to 30 mg DIG-0265C 30 mg of cysteine engineered antibody in PBS at 5.0 mg/mi will be used for conjugation to HDP 30.2115

Adjust antibody solution to 1 mM EDTA:
6 ml antibody solution (30 mg)+60 µl 100 mM EDTA, pH 8.0 Amount antibody: $2.05 \times 10^{-7}$ mol Uncapping of cysteines by reaction of antibody with 40 eq. TCEP:
6 ml antibody solution ($2.05 \times 10^{-7}$ mol)+164 µl 50 mM TCEP solution ($8.21 \times 10^{-6}$ mol)

Incubate for 3 h at 37° C.

Purify each antibody from TCEP by two consecutive dialyses at 4° C. in 2.0 l 1×PBS, 1 mM EDTA, pH 7.4 in a Slide-A-Lyzer Dialysis Cassette 20,000 MWCO, first dialysis ca. 4 h, second dialysis overnight.

Oxidation by reaction of antibody with 20 eq. dehydroascorbic acid (dhAA);
ca. 6 ml antibody solution ($2.05 \times 10^{-7}$ mol)+82 µl fresh 50 mM dhAA solution ($4.1 \times 10^{-6}$ mol)

Incubate for 3 h at RT.

Conjugation with amanitin using 6 eq. HDP 30.2115 and quenching with 25 eq. N-acetyl-L-cysteine:
Solubilize 2.0 mg HDP 30.2115 in 200 µl DMSO=10 µg/µl
ca, 6 ml antibody solution (=ca. 29 mg; $1.98 \times 10^{-7}$ mol)+ 156 µl HDP 30.2115 (=1563 µg; $1.19 \times 10^{-6}$ mol).

Incubate 1 h at RT.

Quench by addition of 49.6 µl 100 mM N-acetyl-L-cysteine ($4.96 \times 10^{-6}$ mol).

Incubate 15 min at RT (or overnight at 4° C.).

Centrifuge at full speed for app. 3 min, take supernatant and measure volume exactly for preparative FPLC.

Purify each reaction mix by preparative FPLC (ÄKTA) using HiLoad 16/600-Superdex 200 µg and an XK-16 column, equilibrated with 1×PBS, pH 7.4 (1.0 ml/min); collect fractions by UV absorption at 280 nm.

Dialysis of the antibody solution at 4° C. overnight in 1×3.0 l PBS, pH 7.4 and Slide-A-Lyzer Dialysis Cassettes 20'000 MWCO.

Determination of protein concentration using naked antibody vs. ADC adjusted to identical protein concentrations. Adjust protein concentration to 5.0 mg/ml(=$3.42 \times 10^{-5}$ M) and bring to sterile conditions by filtration. Store at 4° C.

The invention claimed is:

1. A conjugate comprising (a) an amatoxin comprising (i) an amino acid 4 with a 6'-deoxy position; and (ii) an amino acid 8 with an S-deoxy position; (b) a target-binding moiety; and (c) a cleavable linker linking said amatoxin and said target-binding moiety, wherein said target-binding moiety is an antibody or antigen-wherein said cleavable linker is an enzymatically cleavable linker selected from: Phe-Lys, Val-Lys, Phe-Ala, PheCit and Val-Cit, and wherein the cleavable linker further comprises a p-aminobenzyl (PAB) spacer between the dipeptides and the amatoxin and wherein the conjugate has the structure I

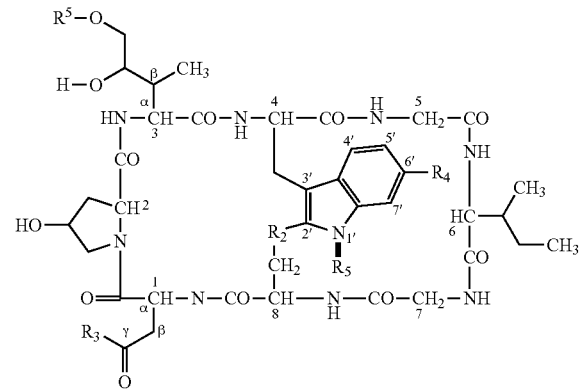

wherein:
$R^2$ is S;
$R^3$ is selected from —$NHR^5$, —NH—$OR^5$, and —$OR^5$;
$R^4$ is H; and
wherein one of $R^5$ is -$L_n$-X, wherein L is a cleavable linker, n is selected from 0 and 1, and X an antibody or antigen-binding fragment thereof, and wherein the remaining $R^5$ are H.

2. A pharmaceutical composition comprising the conjugate of claim 1.

3. A construct comprising (a) an amatoxin comprising (i) an amino acid 4 with a 6'-deoxy position; and (ii) an amino acid 8 with an S-deoxy position; and (c) a cleavable linker moiety carrying a reactive group Y for linking said amatoxin to a target-binding moiety, wherein said target-binding moiety is an antibody or antigen-binding fragment thereof, and wherein said cleavable linker is an enzymatically cleavable linker selected from Phe-Lys, Val-Lys, Phe-Ala, PheCit and Val-Cit, and wherein the cleavable linker further comprises a p-aminobenzyl (PAB) spacer between the dipeptides and the amatoxin and wherein the construct has the structure II

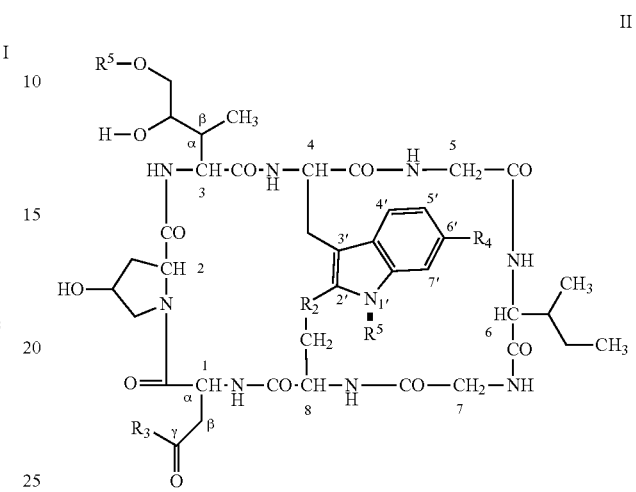

wherein:
$R^2$ is S;
$R^3$ is selected from $NHR^5$, —NH —$OR^5$, and $OR^5$;
$R^4$ is H; and
wherein one of $R^5$ is -L-Y, wherein L is said cleavable linker, and Y is a reactive group for linking said construct to a target-binding moiety.

4. A method for treating cancer, comprising administering the conjugate according to claim 1 to a patient having cancer.

5. The method of claim 4, wherein the cancer is selected from breast cancer, pancreatic cancer, cholangiocarcinoma, colorectal cancer, lung cancer, ovarian cancer, prostate cancer, stomach cancer, kidney cancer, malignant melanoma, leukemia, and/or malignant lymphoma.

* * * * *